United States Patent
Vicent Docón et al.

(10) Patent No.: US 11,732,093 B2
(45) Date of Patent: Aug. 22, 2023

(54) CROSS POLYMERS COMPOSED OF POLYSACCHARIDES AND POLYAMINO ACIDS, AND USES THEREOF

(71) Applicant: POLYPEPTIDE THERAPEUTIC SOLUTIONS S.L., Paterna (ES)

(72) Inventors: María Jesús Vicent Docón, Valencia (ES); Vicent Josep Nebot Carda, Valencia (ES); Daniel Morelló Bolumar, Valencia (ES); Richard Marc England, Valencia (ES)

(73) Assignee: POLYPEPTIDE THERAPEUTIC SOLUTIONS S.L., Paterna (ES)

( * ) Notice: Subject to any disclaimer, the term of this patent is extended or adjusted under 35 U.S.C. 154(b) by 601 days.

(21) Appl. No.: 16/634,013

(22) PCT Filed: Jul. 6, 2018

(86) PCT No.: PCT/EP2018/068327
§ 371 (c)(1),
(2) Date: Jan. 24, 2020

(87) PCT Pub. No.: WO2019/020344
PCT Pub. Date: Jan. 31, 2019

(65) Prior Publication Data
US 2020/0207922 A1    Jul. 2, 2020

(30) Foreign Application Priority Data
Jul. 26, 2017    (EP) .................................... 17382498

(51) Int. Cl.
*C08G 81/00*    (2006.01)
*A61K 47/64*    (2017.01)
*A61K 8/88*    (2006.01)
*C08G 69/10*    (2006.01)

(52) U.S. Cl.
CPC ............... *C08G 81/00* (2013.01); *A61K 8/88* (2013.01); *A61K 47/645* (2017.08); *C08G 69/10* (2013.01); *A61K 2800/10* (2013.01)

(58) Field of Classification Search
CPC ............................. C08G 81/00; C08G 69/10
See application file for complete search history.

(56) References Cited

U.S. PATENT DOCUMENTS

2010/0135935 A1*    6/2010    Leshchiner .......... A61K 8/4973
424/59

FOREIGN PATENT DOCUMENTS

| WO | WO-2006/021644 A1 | 3/2006 | |
| WO | WO-2006021644 A1 * | 3/2006 | ............. A61L 27/20 |
| WO | WO-2013062982 A1 * | 5/2013 | ........... A61K 47/645 |

OTHER PUBLICATIONS

Written Opinion of the International Searching Authority, PCT/EP2018/068327, dated Jun. 7, 2018 (Year: 2018).*
Translation of WO 2006/021644 (Year: 2006).*
Deng, Progress in Polymer Science 39 (2014) p. 330-364 (Year: 2014).*
Agut et al., "Synthesis of Block Copolypeptides by Click Chemistry," Macromolecular Rapid Communications, vol. 29, pp. 1147-1155 (Jan. 2008).
Deng et al., "Functional polypeptide and hybrid materials: Precision synthesis via α-amino acid N-carboxyanhydride polymerization and emerging biomedical applications," Progress in Polymer Science, vol. 39, No. 2, pp. 330-364 (Oct. 2013).
Schatz et al., "Polysaccharide-block-polypeptide Copolymer Vesicles: Towards Synthetic Viral Capsids," Angewandte Chemie International Edition, vol. 48, No. 14, pp. 2572-2575 (Mar. 2009).
Upadhyay et al., "Biomimetic Doxorubicin Loaded Polymersomes from Hyaluronan-block-Poly(γ-benzyl glutamate) Copolymers," Biomacromolecules, vol. 10, No. 10, 2802-2808 (Oct. 2009).
Upadhyay et al., "The intracellular drug delivery and anti tumor activity of doxorubicin loaded poly(γ-benzyl $_L$-glutamate)-b-hyaluronan polymersomes," Biomaterials 31, No. 10, pp. 2882-2892 (Apr. 2010).

* cited by examiner

*Primary Examiner* — Robert C Boyle
(74) *Attorney, Agent, or Firm* — Foley & Lardner LLP

(57) ABSTRACT

The present invention relates to cross polymers composed at least of polysaccharides and polyamino acids, and more particularly to hydrogels composed of said cross polymers. The invention also relates to a process for preparing them, as well as their use in the delivery of active agents for pharmaceutical, diagnostic and/or dermo-cosmetic applications.

19 Claims, 14 Drawing Sheets

CROSS POLYMERS COMPOSED OF POLYSACCHARIDES AND POLYAMINO ACIDS, AND USES THEREOF

CROSS-REFERENCE TO RELATED APPLICATIONS

The present application is the U.S. National Stage of International Application No. PCT/EP2018/068327, filed Jul. 6, 2018, and claims priority to European Patent Application No. 17382498.8, filed Jul. 26, 2017.

FIELD OF THE INVENTION

The present invention relates to the field of cross polymers composed of polysaccharides and polyamino acids, as well as hydrogels derived from said cross polymers. The invention also relates to a process for preparing them, as well as their use in the delivery of active agents for pharmaceutical and (dermo-)cosmetic applications, and as cells/tissue culture medium.

BACKGROUND ART

The hydrogels are cross-linked polymeric materials in the form of a three-dimensional network of natural or synthetic origin, which swell in contact with water to form soft and elastic materials and which retain a significant fraction thereof in its structure without dissolve. Hydrogels can be classified into several types according to different physicochemical properties, for example, according to their viscosity: fluids, semi-solids and solids; according to their structure: elastic (such as gelatin) and non-elastic (such as silica gel); depending on the nature of the solid phase: inorganic (such as bentonite magma) and organic (such as carbomers, cellulosic derivatives, poloxamers, etc.). Another classification is based on the nature of the three-dimensional (3D) network joints that constitute them, hydrogels can be physical gels (the 3D network that forms them are formed by non-covalent interactions) and chemical gels (those in which the network is formed by covalent bonds); this last type of bond is very strong and gives rise to cross-linked nets, in which the molecular framework is fixed by the covalent knots of said nets.

Polymeric solids are especially suitable for forming hydrogels due to their long chain structure and the structures they adopt in solution. The flexibility of such chains makes it possible for them to deform and to allow the entry of solvent molecules into their 3D structure.

The most commonly used hydrogels in cosmetics are fluid, elastic hydrogels, which have a solid organic phase, such as polyvinyl alcohol, Carbopol© (formed by carbomer) and cellulose derivatives (such as sodium carboxymethylcellulose, methyl cellulose or hyaluronic acid). Povidone and Pluronic© (formed by poloxamers) are also the most used.

The state of the art describes several documents disclosing reticulated hyaluronic acids and gels comprising them. In many of them the reticulation takes place using poly-lysine. For instance, WO2006021644 describes a reticulated hyaluronic acid, wherein the reticulate agent is poly-lysine. The resulting reticulated hyaluronic acid is less sensitive to different biodegradation factors while being soluble in water; it is used in reconstructive and/or plastic surgery. The reticulated hyaluronic acid is obtained using at least a catalyzer. Document US2001039336 also describes reticulated hyaluronic acid and a gel comprising it, wherein the hyaluronic acid is modified with poly-lysine; it is used as drug delivery.

There is a clear need to develop novel cross polymers composed of polysaccharides and polyamino acids that keep their properties while allow to effectively transport active agents, especially, through the skin.

SUMMARY OF THE INVENTION

The problem to be solved by the present invention is to provide a biocompatible cross polymer capable of incorporating components for their use as drug delivery and in (dermo-)cosmetics, including their use for the preparation of hydrogels for their topical administration.

The difference between the cross polymers of the present invention and those disclosed in the state of the art is that the cross polymers of the present invention do not comprise polycationic homo-polyamino acids. Surprisingly, the cross polymers disclosed in the present invention show unexpected properties, in particular, increased cell and tissue proliferation and skin permeation. Also, unexpectedly, the cross polymers of the present invention act as permeation enhancers, while providing a resistance to degradation by the action of hyaluronidase. In addition, the cross polymers of the present invention are found to stick to the stratum corneum providing a source for slow release and permeation of the cross polymer to the epidermal layer. Even though cross-linked hyaluronic acid has been widely described, usually 1,4-butanediol diglycidyl ether and divinyl sulfone are used as cross-linking agents. What is particularly relevant is the fact that the cross-polymers of the present invention obtained through the cross-linking of anionic polysaccharides and polyamino acids uses biocompatible chemistries resulting in fully biocompatible and biodegradable materials capable to modulate rheological properties. The use of such cross polymers as drug delivery vehicles or in combination with other carriers, acting as a permeation enhancer has not been previously described. It is also noteworthy the surprising compatibility of the cross polymers of the present invention with water-in-oil (W/O) and oil-in-water (O/W) emulsions, a fact that opens their applicability in conventional topical formulations resulting in a highly versatile vehicle for (dermo-)cosmetic and pharmaceutical applications (e.g. creams, lotions, hydrogels . . . ).

As deeply showed in the present disclosure, the inventors have realized that, surprisingly, by carefully controlling the conditions of cross-linking reaction of the cross polymers of the present invention, and hence the composition of the final cross polymer, a fine tuning of their viscoelastic properties can be achieved. On one hand, the inventors have realized that side chains from the polypeptide backbone within the cross polymers disclosed in the state of the art are either not relevant or fully saturated for the cross-linking. Thus, it has been found that the side functionalities of the amino acids of the polyamino acids play an important role in the interaction with biological barriers and hence the drug delivery properties. Accordingly, another advantage of the present invention is the versatility of the cross polymer in the sense that specific amino acids can be used in the polypeptide sequences as a protease substrate to modulate release applications, e.g. substrate for matrix metalloproteinases in acute inflammation which degrades faster and releases active agents; or the use as cross-linking agents, amino acids precursors of the generation of collagen or other components of the extracellular matrix that is interesting in (dermo-)cosmetics. The cross-linking technology disclosed herein allows e.g. to control the increase in the molecular weight of the starting hyaluronic acid, so that hyaluronic cross-linked hydrogels can be produced accordingly.

Thus, in a first aspect, the invention relates to a cross polymer comprising a recurring unit of formula (I) below:

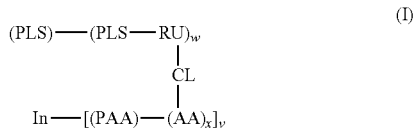

Or its salt, solvate or isomer, wherein: PLS is a radical of a polysaccharide; PLS-RU is a radical of a repeating unit of the polysaccharide; PAA is a radical of a polyamino acid, wherein the polyamino acid is selected from the group consisting of a homo-, a random and a block co-polyamino acid, with the proviso that the homo-polyamino acid is not polycationic; AA is a radical of an amino acid unit of the polyamino acid; subscript x of the radical (AA) is an integer ranging from 1 to 200; subscript v of the radical [(PAA)-(AA)$_x$] is an integer ranging from 1 to 48; subscript w of the radical (PLS-RU) is an integer ranging from 1 to 200; In is a ROP initiator which comprises a terminal X group per each [(PAA)-(AA)] radical, wherein each terminal X group is directly bound to each [(PAA)-(AA)] radical, and wherein the terminal X group is selected form the group consisting of —NH—, —O—, —S—, or combinations thereof; CL is a radical selected from the group consisting of: $(C_1$-$C_{500})$-alkyl, wherein two or more H are substituted by: (1) $(C_1$-$C_{500})$-alkyl, (2) $(C_3$-$C_{30})$-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) $N(H)NH_2$, (12) $R_gCOR_h$, (13) $COOR_i$, (14) $CON(R_j)(R_k)$, (15) $R_lN(R_m)CON(R_n)(R'_n)$, (16) $(C_1$-$C_{30})$-alkene, (17) $(C_1$-$C_{30})$-alkyne, (18) $N_3$, (19) $R_oCH(OR_p)(OR_q)$, (20) $R_rCH(SR_s)(SR_t)$, (21) $R_uB(OR_v)(OR_w)$, (22) $COR_x$; and wherein none, one or more C, are independently replaced by $(C_3$-$C_{30})$-cycloalkyl, aryl, aryl-$(C_1$-$C_{30})$-alkyl, $NR_yR_z$, CO, O, S, S(O), $S(O_2)$, B, P and $(O$—$CH_2$—$CH_2)_A$; subscript A of the radical $(O$—$CH_2$—$CH_2)$ is an integer number between 1 and 500; $R_a$, $R_b$, $R_c$, $R_d$, $R_e$, $R_f$, $R_h$, $R_i$, $R_j$, $R_k$, $R_m$, $R_n$, $R'_n$, $R_p$, $R_q$, $R_s$, $R_t$, $R_v$, $R_w$, $R_x$, $R_y$ and $R_z$ are radicals independently selected from the group consisting of H, $(C_1$-$C_{30})$-alkyl, $(C_1$-$C_{30})$-alkylphenyl, phenyl-$(C_1$-$C_{30})$-alkyl, and $(C_3$-$C_8)$-cycloalkyl; wherein, in any of them, except for H, one or more carbons are optionally substituted by a heteroatom selected from the group consisting of O, S, S(O), $S(O_2)$, halide, N, NH, P, and CO; $R_g$, $R_l$, $R_o$, $R_r$ and $R_u$ are radicals independently selected from the group consisting of $(C_1$-$C_{30})$-alkyl, $(C_1$-$C_{30})$-alkylphenyl, phenyl-$(C_1$-$C_{30})$-alkyl, and $(C_3$-$C_8)$-cycloalkyl; wherein, in any of them, one or more carbons are optionally substituted by a heteroatom selected from the group consisting of O, S, S(O), $S(O_2)$, halide, N, NH, P, and CO; with the proviso that: (1) CL may be present or not, so that if CL is not present, the PLS-RU radical and the AA radical form a direct stable bond.

As understood by the skilled person in the present context, the term "recurring unit" implies that the cross-polymer comprises at least 2 recurring unit.

As understood by the skilled person in view of his common generally knowledge and the technical teaching herein—in practice may a cross-polymer of the present invention normally comprise from 2 to 200 recurring units.

In a further aspect, the invention relates to a conjugate comprising the cross polymer of the invention and at least an active agent which is bound to the cross polymer.

In a further aspect, the present invention relates to a kit comprising the conjugate of the invention.

In another aspect, the present invention relates to the use of the conjugate of the invention as an imaging agent.

In a further aspect, the present invention relates to a pharmaceutical, diagnostic or theranostic composition comprising the conjugate of the invention, and one or more pharmaceutically, diagnostically and theranostically acceptable excipients or carriers, respectively.

In a further aspect, the present invention relates to the conjugate or the pharmaceutical composition of the invention for use in medicine or therapy.

In still another aspect, the present invention relates to the conjugate or the diagnostic composition of the invention for use in diagnostics.

In still another aspect, the present invention relates to the conjugate or the pharmaceutical or diagnostic composition of the invention for use in theranostics.

In a further aspect, the present invention relates to a (dermo-)cosmetic composition comprising the cross polymer or the conjugate of the invention, and one or more cosmetically acceptable excipients.

In a further aspect, the present invention relates to a culture medium for cells and/or tissues comprising the cross polymer of the invention.

In yet another aspect, the present invention relates to a method of culturing cells and/or tissues comprising culturing said cells and/or tissues in the culture medium of the invention.

These and other objects of the present invention will be further described in detail in the description of the invention section that follows, and they are not intended to be limiting to the present invention. Unless otherwise predefined, all technical and scientific terms used herein have the same meaning as commonly understood by the one of ordinary skilled in the art to which the invention belongs. Methods and materials similar or equivalent to those described herein can be used in the practice of the present invention. Throughout the description and claims the word "comprise" and variations of the word, are not intended to exclude other technical features, additives, components, or steps. Additional objects, advantages, and features of the invention will become apparent to those skilled in the art upon examination of the description or may be learned by practice of the invention. Embodiment of the present invention is described below, by way of examples only. The examples are provided by way of illustration, and they are not intended to be limiting of the present invention. Furthermore, the present invention covers all possible combinations of particular embodiments described herein.

BRIEF DESCRIPTION OF THE DRAWINGS

FIG. 2 shows the size-exclusion chromatography analysis of [HA]-[PGA]-[Lys] cross polymer obtained in Example 1a.

DETAILED DESCRIPTION OF THE INVENTION

Figure 1:
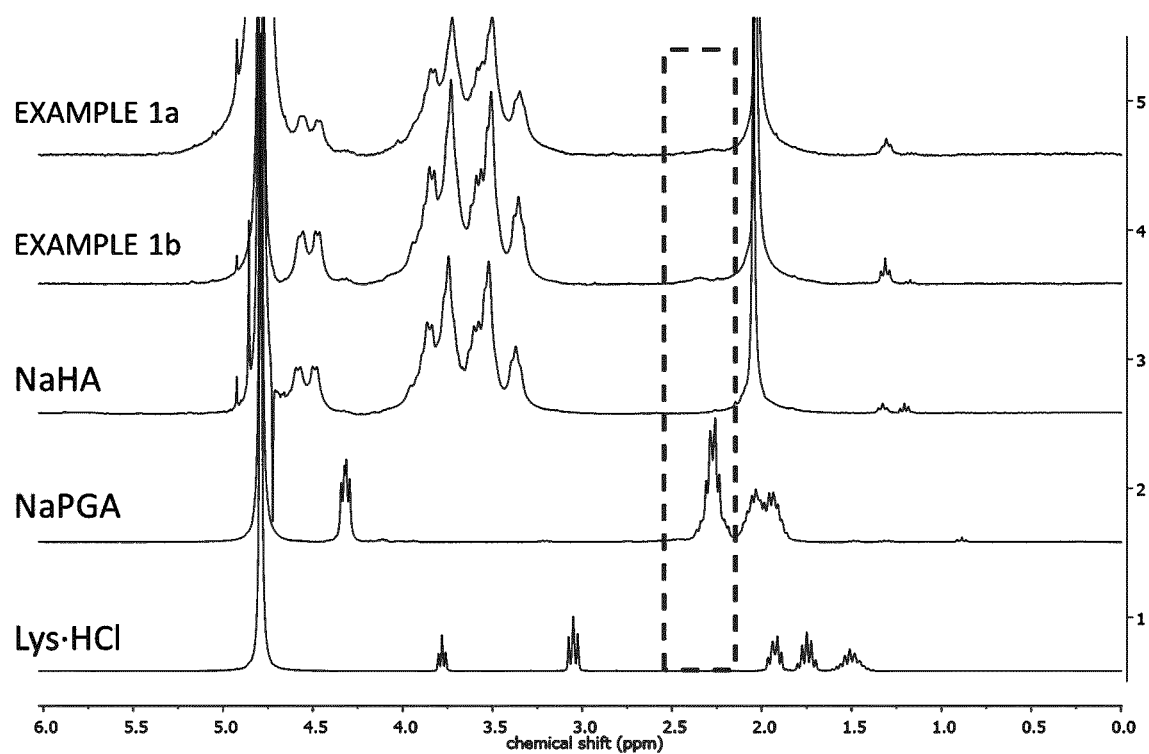
FIG. 1 shows the $^1$H NMR spectra of the raw materials (L-lysine hydrochloride salt (Lys.HCl)), sodium poly-L-glutamate (NaPGA), sodium hyaluronate (NaHA)) and the [HA]-[PGA]-[Lys] cross polymers obtained in Examples 1a and 1b.

All terms as used herein, unless otherwise stated, shall be understood in their ordinary meaning as known in the art. Other more specific definitions for certain terms as used in the present application are as set forth below and are intended to apply uniformly thought the description and claims unless an otherwise expressly set out definition provides a broader definition.

Cross Polymers of the Invention

A cross-polymer comprising a recurring unit of formula (I) below:

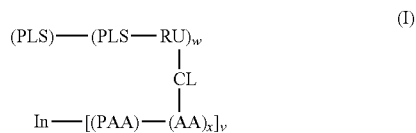

or its salt, solvate or isomer, wherein PLS is a radical of a polysaccharide; PLS-RU is a radical of a repeating unit of the polysaccharide; PAA is a radical of a polyamino acid, wherein the polyamino acid is selected from the group consisting of a homo-, a random and a block co-polyamino acid, with the proviso that the homo-polyamino acid is not polycationic; AA is a radical of an amino acid unit of the polyamino acid; subscript x of the radical (AA) is an integer ranging from 1 to 200; subscript v of the radical [(PAA)-(AA)$_x$] is an integer ranging from 1 to 48; subscript w of the radical (PLS-RU) is an integer ranging from 1 to 200; In is a ROP initiator which comprises a terminal X group per each [(PAA)-(AA)] radical, wherein each terminal X group is directly bond to each [(PAA)-(AA)] radical, and wherein the terminal X group is selected form the group consisting of —NH—, —O—, —S—, or combinations thereof; CL is a radical selected from the group consisting of: $(C_1$-$C_{500})$-alkyl, wherein two or more H are substituted by: (1) $(C_1$-$C_{500})$-alkyl, (2) $(C_3$-$C_{30})$-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, CH$_2$, CO, O, S, N and NH, (4) OH, (5) NR$_a$R$_b$, (6) ONR$_c$R$_d$, (7) CN, (8) halide, (9) SH$_2$, (10) SR$_e$R$_f$, (11) N(H)NH$_2$, (12) R$_g$COR$_h$, (13) COOR$_i$, (14) CON(R$_j$)(R$_k$), (15) R$_l$N(R$_m$)CON(R$_n$)(R'$_n$), (16) $(C_1$-$C_{30})$-alkene, (17) $(C_1$-$C_{30})$-alkyne, (18) N$_3$, (19) R$_o$CH(OR$_p$)(OR$_q$), (20) R$_r$CH(SR$_s$)(SR$_t$), (21) R$_u$B(OR$_v$)(OR$_w$), (22) COR$_x$; and wherein none, one of more C, are independently replaced by $(C_3$-$C_{30})$-cycloalkyl, aryl, aryl-$(C_1$-$C_{30})$-alkyl, NR$_y$R$_z$, CO, O, S, S(O), S(O$_2$), B, P and (O—CH$_2$—CH$_2$)$_A$; subscript A of the (O—CH$_2$—CH$_2$) radical is an integer number between 1 and 500; R$_a$, R$_b$, R$_c$, R$_d$, R$_e$, R$_f$, R$_h$, R$_i$, R$_j$, R$_k$, R$_m$, R$_n$, R'$_n$, R$_p$, R$_q$, R$_s$, R$_t$, R$_v$, R$_w$, R$_x$, R$_y$ and R$_z$ are radicals independently selected from the group consisting of H, $(C_1$-$C_{30})$-alkyl, $(C_1$-$C_{30})$-alkylphenyl, phenyl-$(C_1$-$C_{30})$-alkyl, and $(C_3$-$C_8)$-cycloalkyl; wherein, in any of them, except for H, one or more carbons are optionally substituted by a heteroatom selected from the group consisting of O, S, S(O), S(O$_2$), halide, N, NH, P, and CO; R$_g$, R$_l$, R$_o$, R$_r$ and R$_u$ are radicals independently selected from the group consisting of $(C_1$-$C_{30})$-alkyl, $(C_1$-$C_{30})$-alkylphenyl, phenyl-$(C_1$-$C_{30})$-alkyl, and $(C_3$-$C_8)$-cycloalkyl; wherein, in any of them, one or more carbons, are optionally substituted by a heteroatom selected from the group consisting of O, S, S(O), S(O$_2$), halide, N, NH, P, and CO; with the proviso that: (1) CL may be present or not, so that if CL is not present, the PLS-RU radical and the AA radical form a direct stable bond. When herein referring to the cross polymer, if applicable, it is also referred to the corresponding pharmaceutically acceptable salt or solvate thereof.

In a particular embodiment of the cross polymer described above, the subscript v is an integer between 1 and 5 and each X terminal group is —NH—.

The term "polyamino acid (polymer)" (or PAA), as used herein, refers to a polymer made up at least two repeating units of amino acids. The amino acids of a polyamino acid may be L- or D-amino acids. However, unless otherwise stated, the amino acids of the polyamino acid of the present invention are L-amino acids.

The polyamino acid of the cross polymer of the invention may consists of only one type of amino acidic repeating unit, referred herein, as homo-polyamino acid. The term "poly-cationic" homo-polyamino acid, when used herein, refers to a homo-polyamino acid wherein the amino acidic repeating unit is selected from the group consisting of lysine, ornithine, histidine, proline and arginine.

Alternatively, the polyamino acid of the cross polymer of the invention may consists of more than one type of amino acid as repeating unit, referred herein as co-polyamino acid.

The terms "random co-polyamino acid" and "block co-polyamino acid", as used herein, refer to a co-polyamino acid wherein the different amino acids are linked in a random or sequential way (for instance, LAVILLA, C. et al., 2016), respectively. An example of a random polyaminoacid is the glatimarer acetate (ROBIN, Y, 2015).

The term "peptide bond", as used herein, refers to a covalent chemical bond linking two consecutive amino acid monomers along a (poly)peptide, polyamino acid or protein chain.

The term "polysaccharide", as used herein, refers to a polymeric carbohydrate molecule composed of more than 10 monosaccharide bound together by glycosidic linkages. They range in structure from linear to highly branched. The polysaccharides include, without limitation, glycosaminoglycans, dextran and derivative thereof, cellulose and derivatives thereof (e.g., methylcellulose, hydroxy-propyl-cellulose, hydroxypropylmethylcellulose, carboxymethyl-cellulose, cellulose acetate phthalate, cellulose acetate, succinate, cellulose acetate butyrate, hydroxypropylmethyl-cellulose phthalate), chitosan and derivatives thereof, glucan, arabinoxylans, carrageenans, pectin, glycogen, fucoidan, pentosan, alginate, or cyclodextrins, or their salts and derivatives, including esters and sulfates, thereof.

The term "glycosaminoglycan", as used herein, refers to long unbranched polysaccharides consisting of a repeating disaccharide, wherein the repeating unit (except for keratan) consists of an amino sugar (N-acetylglucosamine or N-acetylgalactosamine) along with an uronic sugar (glucuronic acid or iduronic acid) or galactose. The glycosaminoglycans are classified into four groups, namely, heparin/heparan sulfate, chondroitin sulfate/dermatan sulfate, keratan sulfate and hyaluronic acid.

The term "hyaluronic acid", as used herein, encompasses all variants and combinations of variants of hyaluronic acid, hyaluronate or hyaluronan, of various chain lengths and charge states.

Homo-polysaccharides are polysaccharides composed of a single type of monosaccharide, in other words, the repeating unit is a monosaccharide. Hetero-polysaccharides are polysaccharides composed of two or more different types of monosaccharides, in other words, the repeating unit is two or more different kinds of monosaccharides.

The term "oligosaccharide", as used herein, refers to a polymeric carbohydrate molecule (or poly-saccharide) composed of from 2 to 10 monosaccharides bound together by glycosidic linkages.

The term "monosaccharide", as used herein, refers to a simple form of a sugar that consist of a single saccharide unit which cannot be further decomposed to smaller saccharide building blocks. Preferred monosaccharides for the polysaccharide are selected from the group consisting of furanose, fructose, glucose, galactose, mannose, a modified monosaccharide, such as, and without limitation, sialic acid and eritrose, and mixtures thereof. The monosaccharide may be in its lineal or cyclic form (i.e. hemiacetal cyclic isomers).

In the context of the present invention, the following terms have the meaning detailed below:

The term "alkyl" refers to a straight or branched hydrocarbon radical having the number of carbon atoms if indicated and which is joined to the rest of the molecule by a single bond. For instance, $(C_1\text{-}C_6)$-alkyl, includes but is not limited to, methyl, ethyl, propyl, isopropyl, butyl, isobutyl, sec-butyl, tert-butyl, isopentyl, hexyl, etc.

The term "alkene" refers to a straight or branched unsaturated hydrocarbon radical having the number of atoms indicated that contains at least one carbon-carbon double bond The term "alkyne" refers to a straight or branched unsaturated hydrocarbon radical having the number of atoms indicated that contains at least one carbon-carbon triple bond The term "alkoxy" refers to a moiety having the formula —OR, wherein R is an alkyl group as defined above. Examples of alkoxy groups include, without limitation, methoxy, ethoxy, and isopropyloxy The term "amine" refers to a moiety —$NR_3$, wherein each R group is H or alkyl as defined above; an amino moiety can be ionized to form the corresponding ammonium cation The term "amide" refers to a moiety —NRC(O)R or —C(O)$NR_2$, wherein each R group is H or alkyl, as defined above The term "acyl" refers to a moiety derived by the removal of one or more hydroxyl groups from an oxoacid including inorganic acids; the acyl contains a double bonded oxygen atom and an alkyl group as defined above The term "alkylamine" refers to an alkyl as defined above, wherein one or more hydrogen is replaced by an amino as defined above. Examples of alkylamine groups include, without limitation, methylamine, ethylamine, and isopropylamine The term "halide" refers to fluoride, chloride, bromide or iodide The term "aryl" refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g. benzocyclohexyl) or tricyclic groups, or linked by a bond to form a biaryl group. Representative aryl groups include phenyl, naphthyl, and diphenyl. Other aryl groups include benzyl, having a methylene linking group. Some aryls can be "substituted" or "unsubstituted". "Substituted aryl" refers to aryl groups substituted by one or more groups selected from halide, OH, amino, alkylamine, amide, acyl, $NO_2$, CN, alkyl and alkoxy. If indicated the aryl may have one or more carbons replaced by e.g. a heteroatom; they include, without limitation, pyrrole, pyridine, imidazole, pyrazole, tri-azole, tetrazole, pyrazine, pyrimidine, pyridazine, tri-azine (1,2,3-, 1,2,4- and 1,3,5-isomers), thiphene, furan, thiazole, isothiazole, oxazole and isoxazole. If they are fused to an aromatic ring system, such as phenyl, they include, without limitation, benzopyrroles, benzopyridines, and benzopyrazines The term "alkyl-aryl" refers to an aryl group that is bonded to a compound via an alkyl having the number of carbons indicated The term "cycloalkyl" refers to saturated or partially saturated monocyclic, fused bicyclic or bridged polycyclic ring assembly containing the number of atoms indicated. Saturated monocyclic cycloalkyl rings include for example, cyclopropyl, cyclobutyl, cyclopentyl, cyclohexyl and cyclooctyl. Saturated bicyclic and polycyclic rings include, for example, bicyclooctane. Cycloalkyl groups can also be partially saturated, having one or more double or triple bonds in the ring. Representative cycloalkyl groups that are partially unsaturated include, but are not limited to, cyclobutene, cyclopentene, cyclohexene, cyclohexadiene, cycloheptene, cycloheptadiene, cyclooctene and cyclooctadiene. When cycloalkyl is a saturated monocyclic one, exemplary groups of $C_3$-$C_8$ cycloalkyl include but are not limited to cyclopropyl, cyclobutyl, cyclopentyl, cyclohexyl, cycloheptyl and cyclooctyl. Similarly, exemplary groups of saturated monocyclic ($C_3$-$C_6$)-cycloalkyl, include, but are not limited, to cyclopropyl, cyclobutyl, cyclopentyl, and cyclohexyl. Cycloalkyl groups can be substituted or unsubstituted. Substituted cycloalkyl groups can be substituted with one or more groups selected from halide, OH, amino, alkylamino, amido, acyl, $NO_2$, CN, alkyl and alkoxy. If indicated the cycloalkyl may have one or more carbons replaced by e.g. a heteroatom. If monocyclic, they include, without limitation, aziridine, azetidine, pyrrolidine, piperidine, azepane, azocane, pyrazolidine, imidazolidinie, piperazine (1,2-, 1,3- and 1,4-isomers), tetrahydrofuran, oxane, oxazolidine, dioxane or dithiane. If saturated, they include, without limitation, azetidinyl, pyrrolidinyl, piperidinyl, morpholine, oxetanyl, tetrahydrofuranyl, or tetrahydropyranyl. If unsaturated, they include, without limitation, 2,3-dihydrofuranyl, 2,5-dihydrofuranyl, 3,4-dihydropyranyl, 3,6-dihydropyranyl, or 1,4-dihydropyridinyl The term "azide" refers to the anion with the formula $N_3^-$ The term "carbamate" refers to a —RO—CO—$NR_2$ moiety, wherein each R group is H or alkyl as defined above, and wherein said moiety is derived from the corresponding carbamic acid (i.e. $NH_2COOH$)

The term "Schiff base" refers to a $R_2C$=NR' moiety (wherein each R group is H or alkyl except for R' which cannot be hydrogen). Schiff bases can be considered a sub-class of imines, being either secondary ketimines or secondary aldimines depending on their structure; a number of special naming systems exist for these compounds; for instance, a Schiff base derived from an aniline, where R' is a phenyl or a substituted phenyl, can be called an anil The term "hydrazone" refers to a $R_2C$=$NNH_2$ moiety wherein each R group is an alkyl as defined above The term "maleimide" refers to a $R_2C_2(CO)_2NH$ moiety wherein each R group is H or alkyl as defined above; it also refers to those moieties wherein the NH group is replaced with alkyl or aryl groups as defined above or a polymer such as polyethylene glycol The term "acetal" refers to a $R_2C(OR')_2$ moiety wherein both R' groups are alkyl as defined above. The two OR' groups may be equivalent to each other or not. The two R groups can be equivalent to each other (a "symmetric acetal") or not (a "mixed acetal"), and one or both can be H or alkyl groups as defined above The term "hydrazide" refers to a class of organic compounds sharing a common functional group characterized by a nitrogen to nitrogen covalent bond with 4 substituents with at least one of them being an acyl group. The general structure for a hydrazide is E(=O)—NR—$NR_2$, where the R's are frequently H, wherein the E can be, and the hydrazide are accordingly classified, O, i.e. carbohydrazides (R—C(=O)—NR—$NR_2$), S, i.e. sulfonohydrazides (R—S(=O)$_2$—NR—$NR_2$), and phosphonic dihydrazides (R—P(=O)(—NR—$NR_2$)$_2$.

The polyamino acid of the cross polymer of the present invention comprises an initiator (or "In"). The term "initiator" (or "In"), as used herein, refers to a chemical molecule employed for the initiation of the ring-opening polymerization (ROP) reaction of α-amino acid N-carboxyanhydrides through Normal Amine Mechanism, wherein the initiator is incorporated within the backbone of the resulting polyamino acid (as disclosed, for instance, in DENG, C. et al., 2014; and U.S. Pat. No. 9,623,125B2).

The initiator may contain one or more nucleophilic groups that can initiate the ROP reaction, accordingly, the initiator may be mono- or multifunctional, respectively, resulting in one or several terminal X groups in the cross polymer of the invention, respectively.

In a particular embodiment, optionally in combination with one or more of the various embodiments described above or below, the In has the following chemical structure, W-nucleophilic group(s), wherein W is a radical selected from the group consisting of: ($C_1$-$C_{500}$)-alkyl, wherein one or more H are substituted by: (1) ($C_1$-$C_{500}$)-alkyl, (2) ($C_3$-$C_{30}$)-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) $N(H)NH_2$, (12) $R_gCOR_h$, (13) $COOR_i$, (14) $CON(R_j)(R_k)$, (15) $R_lN(R_m)CON(R_n)(R'_n)$, (16) ($C_1$-$C_{30}$)-alkene, (17) ($C_1$-$C_{30}$)-alkyne, (18) $N_3$, (19) $R_oCH(OR_p)$ $(OR_q)$, (20) $R_rCH(SR_s)(SR_t)$, (21) $R_uB(OR_v)(OR_w)$, (22) $COR_x$; and wherein none, one or more C, are independently replaced by ($C_3$-$C_{30}$)-cycloalkyl, aryl, aryl-($C_1$-$C_{30}$)-alkyl, $NR_yR_z$, CO, O, S, S(O), S(O$_2$), B, P and (O—$CH_2$—$CH_2$)$_A$; subscript A of the radical (O—CH2-CH2) is an integer number between 1 and 500; $R_a$, $R_b$, $R_c$, $R_d$, $R_e$, $R_f$, $R_h$, $R_i$, $R_j$, $R_k$, $R_m$, $R_n$, $R'_n$, $R_p$, $R_q$, $R_s$, $R_t$, $R_v$, $R_w$, $R_x$, $R_y$ and $R_z$ are radicals independently selected from the group consisting of H, ($C_1$-$C_{30}$)-alkyl, ($C_1$-$C_{30}$)-alkylphenyl, phenyl ($C_1$-$C_{30}$)-alkyl and ($C_3$-$C_8$)-cycloalkyl; wherein in any of them, except for H, one or more carbons are optionally substituted by a heteroatom selected from the group consisting of O, S, S(O), S(O$_2$), halide, N, NH, P, and CO; $R_g$, $R_l$, $R_o$, $R_r$ and $R_u$ are radicals independently selected from the group consisting of ($C_1$-$C_{30}$)-alkyl, ($C_1$-$C_{30}$)-alkylphenyl, phenyl, ($C_1$-$C_{30}$)-alkyl, and ($C_3$-$C_8$)-cycloalkyl; wherein, one or more carbons are optionally substituted by a heteroatom selected from the group consisting of O, S, S(O), S(O$_2$), halide, N, NH, P, and CO.

In a particular embodiment, optionally in combination with one or more of the various embodiments described above or below, the initiator has as nucleophilic group an amine, resulting in —NH— as the X terminal group of the cross polymer of the invention.

In another particular embodiment, optionally in combination with one or more of the various embodiments described above or below, the initiator has as nucleophilic group a hydroxyl, resulting in a —O— as the X terminal group of the cross polymer of the invention.

In another particular embodiment, optionally in combination with one or more of the various embodiments described above or below, the initiator has as nucleophilic group a thiol, resulting in a —S— as the X terminal group of the cross polymer of the invention.

In a particular embodiment, optionally in combination with one or more of the various embodiments described above or below, the initiator has 2, 3, 4, 5, 6, 7, and 8 nucleophilic groups that initiate the ROP reaction simultaneously.

In a particular embodiment, optionally in combination with one or more of the various embodiments described above or below, the initiator is selected from the group consisting of ($C_1$-$C_{500}$)-alkyl amine (e.g. butylamine, propylamine, ethylamine, etc.), ethylene glycol and polyethylene glycol from n=2 to n=16, wherein n is the number of repeating ethylene glycol units, with a terminal amine as the nucleophilic group.

In a particular embodiment, optionally in combination with one or more of the various embodiments described above or below, the initiator has between 1 and 5 nucleophilic groups (or the subscript v of the formula I of any of the cross polymers of the present invention) or v is an integer between 1 and 5, and the nucleophilic group of the initiator is —$NH_2$.

The term "linker molecule", as used herein, either refers to a molecule having a first chemical group that reacts with one or more functional groups on a polysaccharide and a second chemical group that reacts to one or more functional groups on a polyamino acid, resulting in a so called "CL" radical of the cross polymer of the present invention.

The chemical groups of the linker molecule and the functional group of the polysaccharide and the polyamino acid are chemically complementary, namely capable to form a stable bond. Said functional group may either refer to an inherent functional group of the polysaccharide or the polyamino acid (i.e. in the case of a naturally occurring polysaccharide or polyamino acid, in other words, a polysaccharide or a polyamino acid present in the nature or living organisms), or a functional group added to the polysaccharide or the polyamino acid, as a result of functionalization prior to their reaction with the corresponding chemical group of the linker molecule (i.e. in the case of a non-naturally occurring polysaccharide or polyamino acid, in other words, a polysaccharide or an amino acid not present in the nature or living organisms). The functional groups of the polysaccharide and the polyamino acid that react with the first and second chemical groups of the linker molecule may be the same or different between them.

The chemical group of the linker molecule includes, without limitation, alkynes, azides, reactive disulfides, maleimides, hydrazide, hydrazones, Schiff bases, acetal, aldehydes, carbamates, and reactive esters, or hydrophobic functionalities.

The functional groups of the polysaccharide may be obtained, without limitation by oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulfation; deamidation, optionally followed by deamination or amide formation with new acids; and esterification.

For example, the polysaccharide may be functionalized with succinic acid to obtain a carboxylic acid functional group, which is capable of reacting with a linker molecule having an amine chemical group to form an amide bond.

The functional groups of the polyamino acid may be obtained by coupling them via amino acid side chain functionality, including, without limitation amide formation, reductive amination, esterification, imine formation, thiol-ene reaction, disulfide formation, etc. For example, the polyamino acid may be functionalized with alkynes, azides, reactive disulfides, maleimides, hydrazide, hydrazones, Schiff bases, acetal, aldehydes, carbamates, and reactive esters, or hydrophobic functionalities.

The stable bond may be non-covalent, reversible covalent and irreversible covalent bond. If needed an orthogonal chemistry may be applied to selectively perform the stable bond. The term "non-covalent bond", as used herein, refers to a bond that does not involve the sharing of electrons, but rather involves more dispersed variations of electromagnetic interactions between molecules. The non-covalent bond can be classified into various categories, such as electrostatic interaction, π-interaction, van der Waals forces, hydrogen bonding and hydrophobic effect.

The terms "cross-link", "cross-linked" or "cross-linking", when used herein, refer to a chemical bond of one polymeric chain to another one.

In a particular embodiment, optionally in combination with one or more of the various embodiments described above or below, the CL radical is not present in the cross polymer of the invention.

In another particular embodiment, optionally in combination with one or more of the various embodiments described above or below, the CL radical is present in the cross polymer of the invention.

In another particular embodiment, optionally in combination with one or more of the various embodiments described above or below, the CL radical of the cross polymer of the present invention is selected form the group consisting of:

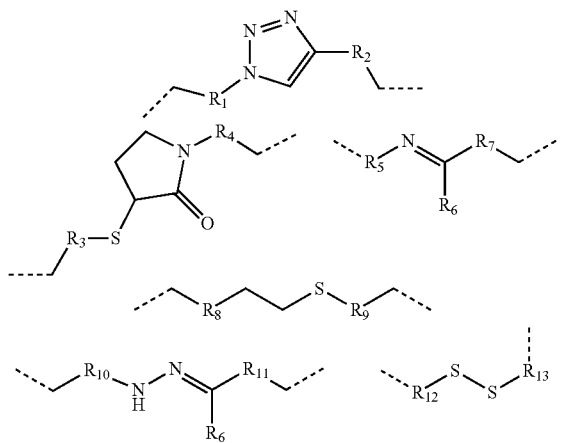

Wherein $R_1$ to $R_5$ and $R_7$ to $R_{13}$ are independently selected from the group consisting of:

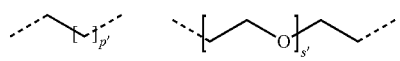

p' and s' are integers independently selected from 0 to 500; and $R_6$ is independently selected from the group consisting of H and $(C_1-C_4)$-alkyl.

In another particular embodiment, optionally in combination with one or more of the various embodiments described above or below, the CL radical of the cross polymer of the present invention is —NH—CH(COOH)—$(C_1-C_{30})$-alkyl-NH—.

In a particular embodiment, optionally in combination with one or more of the various embodiments described above or below, or optionally in combination with the cross polymer of formula (I) as defined above, wherein CL is present or not present, and wherein optionally, v is an integer between 1 and 5 and each X terminal group is —NH—, the PAA radical of the cross polymer of the invention is a radical of formula (II)

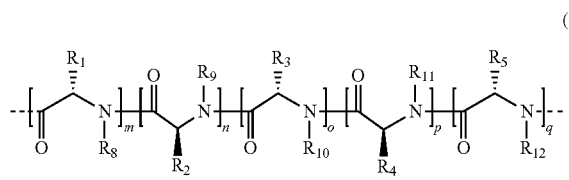

(II)

And the AA radical is a radical of formula (III)

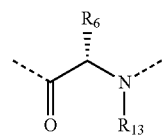

(III)

Wherein m, n, o, p and q are integers independently selected from 0 to 500, and wherein m+n+o+p+q>1; $R_1$ to $R_6$ are independently selected from the group consisting of:

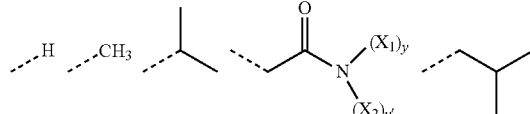

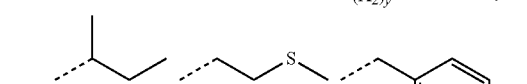

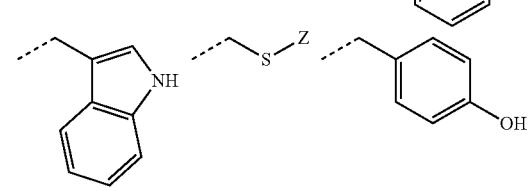

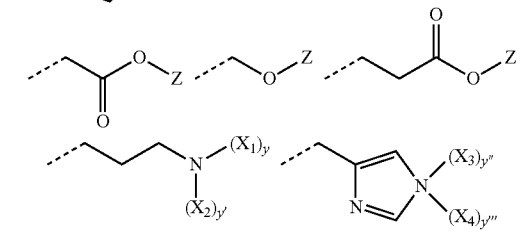

-continued

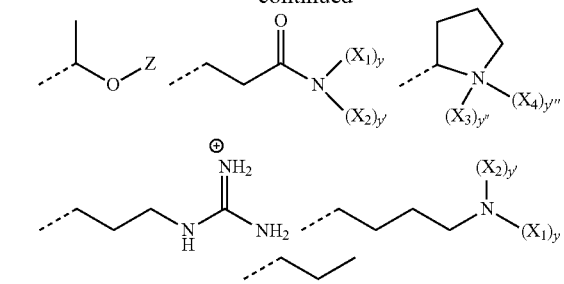

Each $X_1$ and $X_2$ is independently selected from the group consisting of H, N, $NH_2$, and Z; each $X_3$ and $X_4$ is independently selected from the group consisting of H and Z; each y and y' is an integer independently selected from 0 to 3, wherein y+y'=2 or 3; each y'' and y''' is an integer independently selected from 0 to 2, wherein y''+y'''=1 or 2; Z is selected from the group consisting of H, metallic counterion and inorganic counterion; and $R_8$ to $R_{13}$ are independently selected from the group consisting of H and —$C_1$-$C_4$ alkyl; with the provisos that: (1) when CL is not present, the AA radical is bound through a peptidic bond to the PAA radical through the terminal amine of the PAA radical; and (2) when CL is present, the AA radical is bound to CL through the amine terminal of the AA radical.

In another particular embodiment, optionally in combination with one or more of the various embodiments described above or below, or optionally in combination with the cross polymer of formula (I) as defined above, wherein CL is present or not present, and wherein optionally v is an integer between 1 and 5 and each X terminal group is —NH—, the PAA radical of the cross polymer of the invention is a radical of formula (IV)

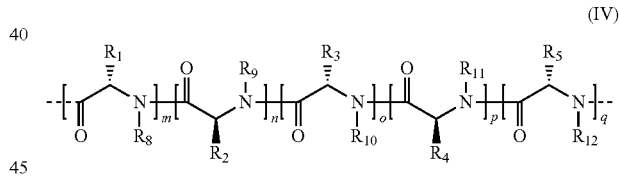

(IV)

And the AA radical is a radical of formula (V)

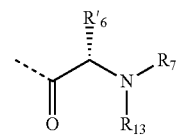

(V)

Wherein, m, n, o, p and q are integers independently selected from 0 to 500, and wherein m+n+o+p+q>1; $R_1$ to $R_5$ are independently selected from the group consisting of:

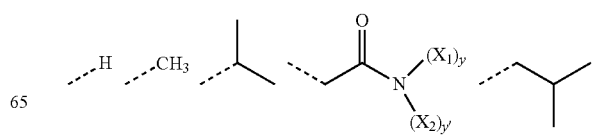

-continued

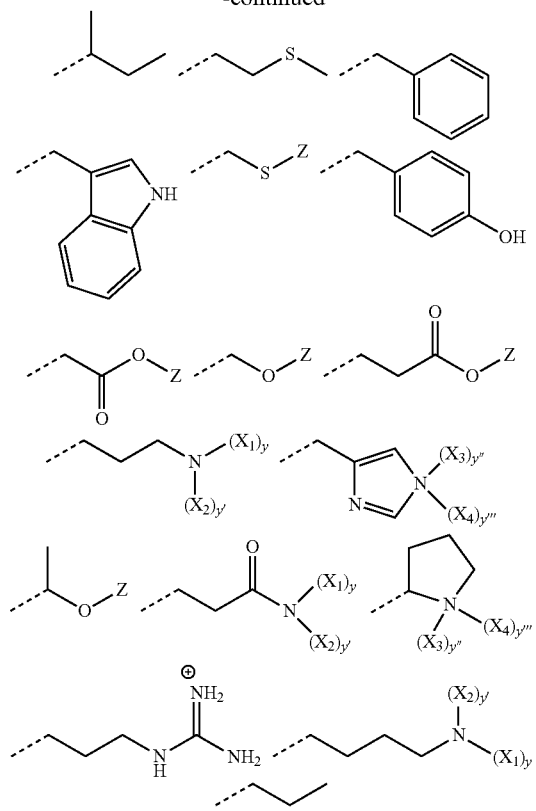

R'$_6$ is selected from the group consisting of:

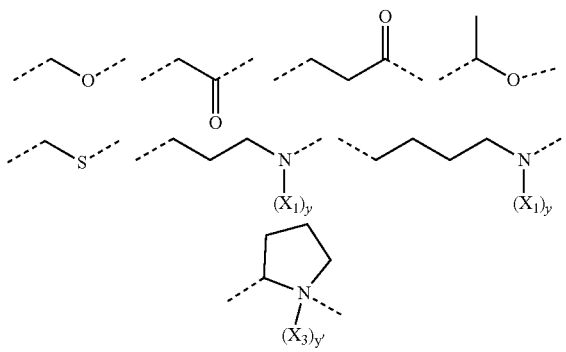

Each X$_1$ and X$_2$ is independently selected from the group consisting of H, N, NH$_2$, and Z; each X$_3$ and X$_4$ is selected from the group consisting of H and Z; each subscript y and y' of R$_1$ to R$_5$ is an integer independently selected from 0 to 3, wherein y+y'=2 or 3; each subscript y" and y''' of R$_1$ to R$_5$ is an integer independently selected from 0 to 2, wherein y"+y'''=1 or 2; each subscript y of R'$_6$ is 1 or 2; subscript y' of R'$_6$ is 0 or 1; Z is selected from the group consisting of H, metallic counterion and inorganic counterion; R$_7$ is a radical selected from the group consisting of: (C$_1$-C$_{500}$)-alkyl, wherein one or more H are substituted by: (1) (C$_1$-C$_{500}$)-alkyl, (2) (C$_3$-C$_{30}$)-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, CH$_2$, CO, O, S, N and NH, (4) OH, (5) NR$_a$R$_b$, (6) ONR$_c$R$_d$, (7) CN, (8) halide, (9) SH$_2$, (10) SR$_e$R$_f$, (11) N(H)NH$_2$, (12) R$_g$COR$_h$, (13) COOR$_i$, (14) CON(R$_j$)(R$_k$), (15) R$_l$N(R$_m$)CON(R$_n$)(R'$_n$), (16) (C$_1$-C$_{30}$)-alkene, (17) (C$_1$-C$_{30}$)-alkyne, (18) N$_3$, (19) R$_o$CH(OR$_p$)(OR$_q$), (20) R$_r$CH(SR$_s$)(SR$_t$), (21) R$_u$B(OR$_v$)(OR$_w$), (22) COR$_x$; and wherein none, one of more C, are independently replaced by (C$_3$-C$_{30}$)-cycloalkyl, aryl, aryl-(C$_1$-C$_{30}$)-alkyl, NR$_y$R$_z$, CO, O, S, S(O), S(O$_2$), B, P and (O—CH$_2$—CH$_2$)$_A$; subscript A of the (O—CH$_2$—CH$_2$) radical is an integer number between 1 and 500; R$_a$, R$_b$, R$_c$, R$_d$, R$_e$, R$_f$, R$_h$, R$_i$, R$_j$, R$_k$, R$_m$, R$_n$, R'$_n$, R$_p$, R$_q$, R$_s$, R$_t$, R$_v$, R$_w$, R$_x$, R$_y$, and R$_z$ are radicals independently selected from the group consisting of H, (C$_1$-C$_{30}$)-alkyl, (C$_1$-C$_{30}$)-alkylphenyl, phenyl (C$_1$-C$_{30}$)-alkyl and (C$_3$-C$_8$)-cycloalkyl; wherein in any of them, except for H, one or more carbons are optionally substituted by a heteroatom selected from the group consisting of O, S, S(O), S(O$_2$), halide, N, NH, P, and CO; R$_g$, R$_l$, R$_o$, R$_r$ and R$_u$ are radicals independently selected from the group consisting of (C$_1$-C$_{30}$)-alkyl, (C$_1$-C$_{30}$)-alkylphenyl, phenyl, (C$_1$-C$_{30}$)-alkyl, and (C$_3$-C$_8$)-cycloalkyl; wherein, one or more carbons are optionally substituted by a heteroatom selected from the group consisting of O, S, S(O), S(O$_2$), halide, N, NH, P, and CO; and R$_8$ to R$_{13}$ are independently selected from the group consisting of H and (C$_1$-C$_4$)-alkyl; with the provisos that: (1) when CL is not present, the AA radical is bound through a peptidic bond to the PAA radical through the terminal amine of the PAA radical; and (2) when CL is present, the radical AA is bound to CL through R'$_6$.

In a particular embodiment, optionally in combination with one or more of the various embodiments described above or below, the R$_7$ radical of the cross polymer of the present invention is selected from the group consisting of H, CO—(C$_1$-C$_{20}$)-alkyl, CONH—(C$_1$-C$_{20}$)-alkyl and pyroglutamate.

In a particular embodiment, optionally in combination with one or more of the various embodiments described above or below, or optionally in combination with the cross polymer as defined above of formulas (I), (II) and (III), wherein CL is present or not present, and wherein v is an integer between 1 and 5 and each X terminal group is —NH—, the polyamino acid of the cross polymer of the present invention is a homo-polyamino acid, wherein R$_1$=R$_2$=R$_3$=R$_4$=R$_5$=R$_6$. In a preferred embodiment, said R$_1$=R$_2$=R$_3$=R$_4$=R$_5$=R$_6$ is selected form the group consisting of:

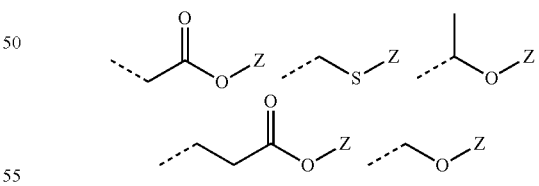

Wherein Z is selected from the group consisting of H, metallic counterion and inorganic counterion.

In another particular embodiment, optionally in combination with one or more of the various embodiments described above or below, or optionally in combination with the cross polymer as defined above of formulas (I), (IV) and (V), wherein CL is present or not present, and wherein v is an integer between 1 and 5 and each X terminal group is —NH—, the polyamino of the cross polymer of the present invention is also a homo-polyamino acid, wherein R$_1$=R$_2$=R$_3$=R$_4$=R$_5$ and R'$_6$ is the corresponding double radical of said $R_1=R_2=R_3=R_4=R_5$. In a preferred embodiment, said $R_1=R_2=R_3=R_4=R_5$ is selected from the group consisting of:

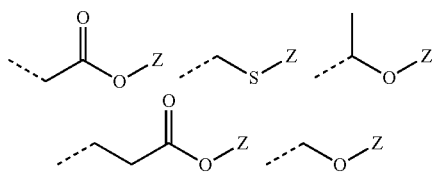

And said $R'_6$ is selected from the group consisting of:

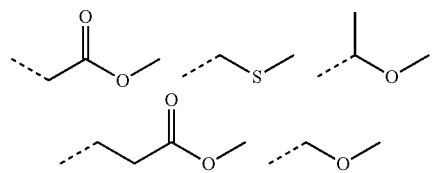

Wherein Z is selected from the group consisting of H, metallic counterion and inorganic counterion.

In another particular embodiment, optionally in combination with one or more of the various embodiments described above or below, or optionally in combination with the cross polymer as defined above of formulas (I), (II) and (III), wherein CL is present or not present, and wherein v is an integer between 1 and 5 and each X terminal group is —NH—, the polyamino acid of the cross polymer of the invention is a random or block co-polyamino acid. In a preferred embodiment said $R_1, R_2, R_3, R_4, R_5$ and $R_6$ of the random or block co-polyamino acid are independently selected from the group consisting of:

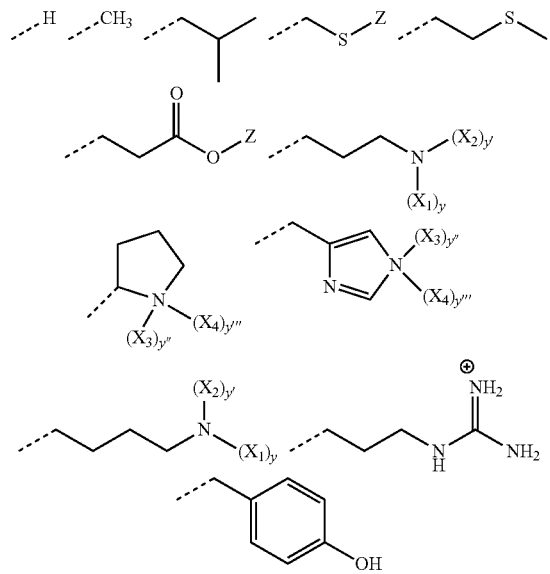

Wherein each $X_1$ and $X_2$ is independently selected from the group consisting of H, N, $NH_2$, and Z; each $X_3$ and $X_4$ is independently selected from the group consisting of H and Z; each y and y' is an integer independently selected from 0 to 3, wherein y+y'=2 or 3; each y" and y'" is an integer independently selected from 0 to 2, wherein y"+y'"=1 or 2; Z is selected from the group consisting of H, metallic counterion and inorganic counterion. In a more preferred embodiment, $R_1, R_2, R_3, R_4, R_5$ and $R_6$ of the random or block polyamino acid of the invention are independently selected from the group consisting of:

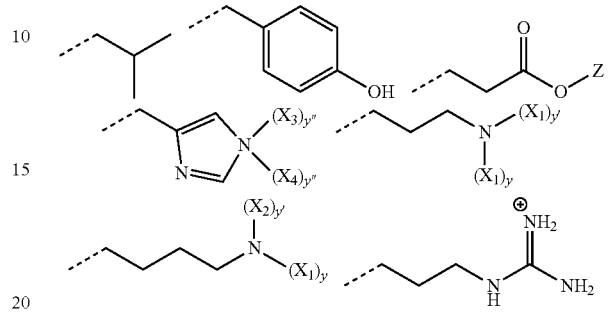

Wherein each $X_1$ and $X_2$ is independently selected from the group consisting of H, N, $NH_2$, and Z; each $X_3$ and $X_4$ is independently selected from the group consisting of H and Z; each y and y' is an integer independently selected from 0 to 3, wherein y+y'=2 or 3; each y" and y'" is an integer independently selected from 0 to 2, wherein y"+y'"=1 or 2; Z is selected from the group consisting of H, metallic counterion and inorganic counterion.

In another particular embodiment, optionally in combination with one or more of the various embodiments described above or below, or optionally in combination with the cross polymer as defined above of formulas (I), (IV) and (V), wherein CL is present or not, and wherein v is an integer between 1 and 5 and each X terminal group is —NH—, the polyamino acid of the cross polymer of the present invention is a random or block co-polyamino acid. In a preferred embodiment, the radicals $R_1$ to $R_5$ of the random or block co-polyamino acid are independently selected from the group consisting of:

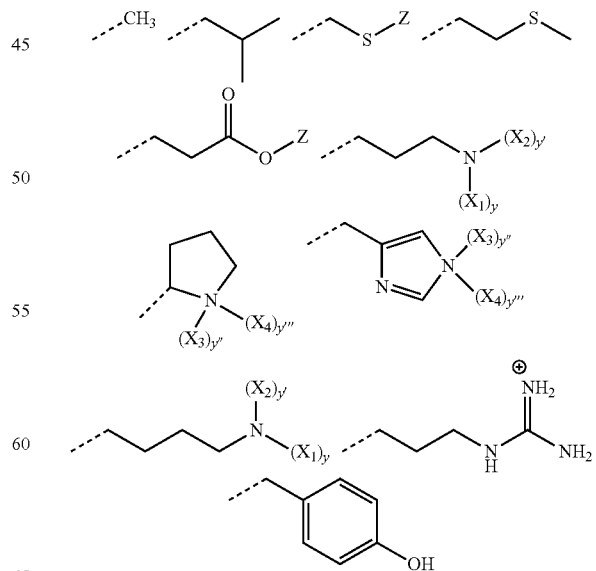

And the radical $R'_6$ is selected from the group consisting of:

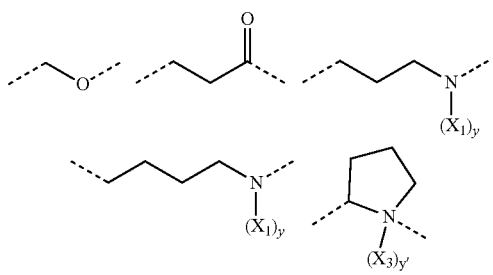

Wherein each $X_1$ and $X_2$ is independently selected from the group consisting of H, N, $NH_2$, and Z; each $X_3$ and $X_4$ is independently selected from the group consisting of H and Z; each subscript y and y' of $R_1$ to $R_5$ is an integer independently selected from 0 to 3, wherein y+y'=2 or 3; each subscript y" and y'" of $R_1$ to $R_5$ is an integer independently selected from 0 to 2, wherein y"+y'"=1 or 2;

each subscript y of $R'_6$ is 1 or 2; subscript y' of $R'_6$ is 0 or 1; and each Z is independently selected from the group consisting of H, metallic counterion and inorganic counterion. In a more preferred embodiment, the radicals $R_1$ to $R_5$ are independently selected from the group consisting of:

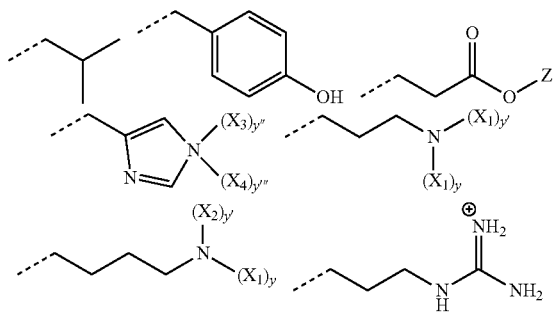

Wherein each $X_1$ and $X_2$ is independently selected from the group consisting of H, N, $NH_2$, and Z; each $X_3$ and $X_4$ is independently selected from the group consisting of H and Z; each subscript y and y' of $R_1$ to $R_5$ is an integer independently selected from 0 to 3, wherein y+y'=2 or 3; each subscript y" and y'" of $R_1$ to $R_5$ is an integer independently selected from 0 to 2, wherein y"+y'"=1 or 2;

each subscript y of $R'_6$ is 1 or 2; subscript y' of $R'_6$ is 0 or 1; and each Z is independently selected from the group consisting of H, metallic counterion and inorganic counterion.

In a particular embodiment, optionally in combination with one or more of the various embodiments described above or below, the polysaccharide of the cross polymer of the present invention is selected from the group consisting of hyaluronic acid, pectin, chitosan and chondroitin sulfate.

In another particular embodiment, optionally in combination with one or more of the various embodiments described above or below, or optionally in combination with the particular embodiment wherein the cross polymer is of formula (I) as defined above, and CL is not present, the polysaccharide of the cross polymer is hyaluronic acid, the PAA is polyglutamate, the AA is glutamate, v is an integer between 2 and 4 and x+w is an integer between 2 and 200.

In a particular embodiment, optionally in combination with one or more of the various embodiments described above, or optionally in combination with the particular embodiment wherein the cross polymer is of formula (I) as defined above, and CL is present, the polysaccharide of the cross polymer is hyaluronic acid, the PAA is polyglutamate, the AA is glutamate, v=1, x+w is an integer between 2 and 200 and the CL is —NH—CH(COOH)—($C_1$-$C_4$)-alkyl-NH—.

Salts, Isomers and Solvates of the Cross Polymers of the Invention

As used herein, the term "salt" refers to acid or base salts of the cross polymer of the present invention. For instance, the cross polymers of the present invention contain one or more basic nitrogens and, therefore, may form salts by reacting with acids, both organic and inorganic. Examples of said salts include without limitation: salts of inorganic acids, such as hydrochloric acid, hydrobromic acid, hydriodic acid, nitric acid, perchloric acid, sulfuric acid or phosphoric acid; and salts of organic acids, such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, amongst others; and salts of quaternary ammonium, such as methyl iodide, ethyl iodide, and the like.

Some cross polymers of the present invention may contain one or more acidic protons and, therefore, may also form salts by reacting with bases. Examples of said salts include, without limitation: salts of inorganic cations, such as sodium, potassium, calcium, magnesium, lithium, aluminium, zinc, etc.; and salts formed with pharmaceutically acceptable amines, such as ammonia, alkylamines, hydroxyalkylamines, lysine, arginine, N-methylglucamine, procaine and similar ones.

There are no limitations as to the types of salts that may be used, provided that they are pharmaceutically acceptable to be used for therapeutic purposes, hence, they are non-toxic. Pharmaceutically acceptable salts are understood to mean those salts which, according to medical criteria, are adequate to be used in contact with human beings' or other mammals' tissues without causing undue toxicity, irritation, allergic responses or similar effects. Pharmaceutically acceptable salts are widely known to a person skilled in the art.

The salts of a cross polymer of the invention may be obtained during the final isolation and purification of the cross polymers of the invention or be prepared by treating a cross polymer of the invention with a sufficient quantity of the desired acid or base to produce the salt in a conventional manner. The salts may, in turn, be converted into other salts by means of ion-exchange using, for example, and without limitation, an ion-exchange resin.

The cross polymers of the invention and the salts thereof may differ in terms of certain physical properties, but, for purposes of the invention, are equivalent. All the salts of cross polymers of the invention are included within the scope of the invention.

The cross polymers of the present invention may form complexes with solvents with which they are made to react or from which they are precipitated or crystallised. These complexes are known as solvates. As used herein, the term "solvate" refers to a complex of variable stoichiometry formed by a solute (a cross polymers of the invention or a salt thereof) and a solvent. Examples of solvents include pharmaceutically acceptable solvents such as, without limitation, water, ethanol and similar ones. A complex formed by water is known as a hydrate. Solvates of the cross polymers of the invention (or the salts thereof), including hydrates, are included within the scope of the invention.

The cross polymers of the invention may exist in different physical forms, i.e. in amorphous form and in crystalline forms. Moreover, the cross polymers of the present invention may be capable of crystallising in more than one form, a characteristic known as polymorphism. Polymorphs may differ in some physical properties widely known to persons skilled in the art, such as, for example, X-ray diffractograms, melting points or solubility. All the physical forms of the cross polymers of the invention, including all the polymorphic forms thereof ("polymorphs"), are included within the scope of the present invention.

Some cross polymers of the present invention may exist in the form of several optical isomers (or stereoisomers) depending on the presence of chiral centres. The single isomers, enantiomers or diastereoisomers and mixtures thereof fall within the scope of the present invention. Similarly, and unless otherwise indicated, the cross polymers of the invention are intended to include cross polymers that only differ in the presence of one or more isotopically enriched atoms. For example, compounds having one or more hydrogens substituted with deuterium or tritium, or having one or more carbons substituted with $^{13}C$- or $^{14}C$-enriched carbon, or one or more nitrogen substituted with $^{15}N$-enriched nitrogen are within the scope of the present invention.

In another aspect, the present invention provides a process for the synthesis of the cross polymers of formula (I) wherein CL is not present and the polysaccharide and the polyamino acid are naturally occurring, the process comprises: (1.1) reaction of the polysaccharide and the polyamino acid through their functional (and complementary) groups via activation of the carboxylic acid and coupling with the reactive amine, wherein the cross-linking degree of the resulting cross polymer is controlled by adjusting the relative molar ratio of activated carboxylic acids to reactive amines and the reaction conditions, namely, temperature, time of reaction and concentration, and (1.2) purification by fractionation, precipitation, ultrafiltration, dialysis, size exclusion chromatography or tangential flow filtration of the reaction product obtained in the previous step. In another aspect, the present invention provides a process for the synthesis of the cross polymers of formula (I) wherein CL is not present and the polysaccharide and/or the polyamino acid are non-naturally occurring, the process comprises, (2.1) the chemical modifications of the polysaccharide and/or the polyamino acid in order to incorporate functional group(s) chemically complementary between them that would react to form a stable bond under the appropriate reaction conditions, and modulation of the degree of cross-linking of the resulting cross polymer through the molar ratios of the functional groups and the reaction conditions, namely, temperature, time of reaction and concentration, and (2.2) purification by fractionation, precipitation, ultrafiltration, dialysis, size exclusion chromatography or tangential flow filtration of the reaction product of obtained in the previous step.

The present invention also provides a process for the synthesis of the cross polymers of formula (I) wherein CL is present and the polysaccharide and the polyamino acid are naturally occurring, the process comprises the following steps: (3.1) reacting the polysaccharide with the polyamino acid using a linker molecule to generate the corresponding CL radical by (3.1.a) dissolving the polysaccharide and the polyamino acid in an aqueous solution (solution A), (3.1.b) adding a carboxylic acid activating group to solution A (solution B), (3.1.c) adding the "linker molecule" to solution B to react with the activated carboxylic acids, and (3.2) purifying the reaction product obtained in step (3.1) by fractionation, precipitation, ultrafiltration, dialysis, size exclusion chromatography or tangential flow filtration. The present invention also provides a process for the synthesis of the cross polymers of formula (I) wherein CL is present and the polysaccharide and/or the polyamino acid are non-naturally occurring ones, the process comprises the following step: (4.1) chemical modifications of the polysaccharide and/or the polyamino acid in order to incorporate functional group(s) chemically complementary with the chemical groups of the linker molecule, (4.2) reacting said chemically modified polysaccharide and polyamino acid with the linker molecule to form stable bonds, and generation of the corresponding CL radical by (4.2.a) dissolving the chemically modified polysaccharide and polyamino acid in an aqueous solution (solution A'), (4.2.b) adding a carboxylic acid activating group to solution A (solution B), (4.2.c) adding the "linker molecule" to solution B' to react with the activated carboxylic acids, (4.3) purifying the reaction product obtained in step (4.2) by fractionation, precipitation, ultrafiltration, dialysis, size exclusion chromatography or tangential flow filtration.

Conjugates

The term "conjugate", as used herein, refers to a combination comprising the cross polymer of the present invention and at least an active agent. Accordingly, the cross polymers of the present invention can be used as drug delivery of active agents, wherein the delivery may be a sustained release or not. Accordingly, the invention relates to a conjugate comprising the cross polymer of the present invention and at least an active agent which is bound to the cross polymer.

In the context of the present invention, the term "active agent" refers to an active pharmaceutical agent, an imaging agent or a cosmetic agent.

The active agent(s) may be covalently bound to the cross polymer either directly or through a connecting group. The term "connecting group", when used herein, refers to an organic moiety that connects or binds the cross polymer of the present invention and at least an active agent, wherein the connecting group may be, independently and without limitation, phosphodiester, phosphorothioate, carbamate, methylphosphonate, guanidinium, disulphides, esters, hydrazones, sulfamate, sulfamide, acetal, formacetal, thioformacetal, sulfone, amide and mixtures thereof. The active agent may be covalently bond to the cross polymer through the polyamino acid, the polysaccharide, or both of them. In a particular embodiment, the covalent bond is a bioresponsive one. The term "bioresponsive bond", as used herein, refers to a chemical link cleavable under specific physiological or external triggers (for example, and without limitation, pH, reactive oxygen species, reductive environment, specific enzymes, glucose, light, temperature, etc.). In a particular embodiment, the at least active agent of the conjugate of the present invention is bound to the cross polymer of the present invention through the PLS-(PLS-RU)$_w$ radical and/or the (PAA)-(AA)$_x$ radical. Alternatively, the active agent can be non-covalently bound to the cross polymer of the present invention.

In a particular embodiment, the at least active agent may be incorporated in the cross polymer of the invention through its encapsulation into micelles, liposomes, polymeric micelles or polymersomes.

In a particular embodiment, the at least active agent of the conjugate of the present invention is selected from the group consisting of active pharmaceutical agent, imaging agent, and combinations thereof.

In a particular embodiment, the at least active pharmaceutical agent is selected from small molecules (i.e. drugs or prodrugs) to biomolecules (i.e. hormones, peptides, (apolipo)proteins, antibodies, Fab or fragment antigen-binding, and nucleic acids or analogues). Examples of active pharmaceutical ingredients include, without limitation, antibody, antigen, arginine-glycine-aspartate peptides (RGDs), bisphosphonate, aptamer, gaptamer, polysaccharide, double stranded oligonucleotide (DNA), siRNA, short hairpin RNA, micro RNA, antisense sequence, ribozyme or RNA enzyme, locked nucleic acid, peptide nucleic acid, intercalating nucleic acid, etc. In a particular embodiment, the active pharmaceutical ingredient is selected from the group consisting of vaccines, antioxidants, anti-inflammatories, neuroprotective, vitamins, UV-filters, ions, metals, growth factors, stem cells, natural extracts, chemotherapeutics, Rho-associated protein kinase (ROCK) inhibitors, proteins, antidotes, analgesics, anesthetics, antidiabetics, antibiotics, antifungals, antihistamines, corticoids, anticancer agents, anti-metastatic agents, anti-apoptotics, pro-apoptotics, neuroprotective agents, immunostimulant agents and immunosupressor agents.

Vitamins include vitamin analogues, vitamin derivatives and modified vitamins, which can be included in the particulates (e.g., microparticles) and compositions of the present disclosure include but are not limited to Vitamin A (and Vitamin A precursors), thiamin (Vitamin B1), riboflavin (Vitamin B2), niacin (Vitamin B3), pyridoxine (Vitamin B6), folic acid, cobalamins (Vitamin B12), Pantothenic acid (Vitamin B5), Vitamin C, Vitamin D, Vitamin E, Biotin, Vitamin K, other B complex vitamins, B complex related compounds such as Choline and Inositol, for example, and carotenoids such as, and without limitation, lutein, lycopene, zeaxanthin, and astaxanthin. It will be understood that derivatives and analogues of vitamins are within the scope of the present disclosure. Analogues contemplated herein include, but are not limited to modification of the ring structure, functional groups or side chains of the vitamin molecule including the additional removal of protecting groups and salts and complexes thereof derived from any source such as being chemically synthesized or identified by screening process such as natural product screening provided that the analogue possesses some binding activity for the vitamin receptor. In a particular embodiment, the vitamin is folate, nicotinamide, N, N-diethylnicotinamide, biotin, or sodium salicylate.

As used herein, the term "imaging agent", refers to any substance that is used as a label, or that enhances specific structures in any imaging technique. An imaging agent, hence, includes optical imaging agent, magnetic resonance imaging agent, radioisotope, and contrast agent. Examples, without limitation, of optical imaging agent are acridine dye, a coumarin dye, a rhodamine dye, a xanthene dye, a cyanine dye, and a pyrene dye, Texas Red, Alexa Fluor® dye, BODIPY® dye, Fluorescein, Oregon Green® dye, and Rhodamine Green™ dye, which are commercially available or readily prepared by methods known to those skilled in the art. Examples of imaging agents appropriate for the present invention include, but are not limited to, transition metals and radioactive transition metals chelated to chelating agents, for instance DTPA (diethylene triamine pentaacetic acid), DOTA (1,4,7,10-Tetraazacyclododecane-1,4,7,10-tetraacetic acid) and NOTA (1,4,7-Triazacyclononane-1,4,7-triacetic acid).

In another particular embodiment, the active agent is a cosmetic agent. As used herein, the term "cosmetic agent" refers to an agent intended to be applied to the human body for cleansing, beautifying, promoting attractiveness, or altering the appearance without affecting the body's structure or functions. The cross polymer alone or the conjugate of the cross polymer and the at least cosmetic agent act by treating and/or preventing the effects of free radicals, including and without limitation, peroxidyzing cutaneous substances, in particular, the membrane lipids of cells such as keratinocytes, inflammation, aging, depigmentation and fineness of skin grains, improving the differentiation of keratinocytes, moisturizing the skin, and also anesthetic action on cutaneous nerve endings.

In another particular embodiment, the at least one cosmetic agent of the conjugates of the present invention is selected from the group consisting of vitamins A, B1, B6, B12, E, C, PP, retinoic acid, retinal, retinol and esters thereof, salicylic acid and derivatives thereof, in particular salts or esters thereof, 2,5-dihydroxybenzoic acid, tocopherol and esters thereof, in particular tocopherol phosphate, asiatic acid, madecassic acid and its glycoside-containing esters, asiaticoside, an extract of Centella asiatica, an extract of Siegesbeckia orientalis, proantocyanide oligomers, in particular those obtained from grape pips, and esters thereof, in particular the palmitic and stearic esters, derivatives of ascorbic acid, in particular its phosphate and its salts, erythorbic acid, oligoelements, in particular in the form of a salt, specifically in the form of an aspartate or a chloride of magnesium, selenium, zinc, or copper, alpha-hydroxylated acids, in particular malic acid, lactic acid, and tartaric acid, and esters thereof, in particular with fatty alcohols, such as stearyl alcohol, amino acids, in particular serine, threonine, citrulline, and amino acids constituting NMF (Natural Moisturizing Factor), ceramides, in particular 2, 3 or 6 ceramides used singly or in a mixture, photoceramides, in particular those extracted from wheat, and ecdysteroids, in particular ecdysterone, and esters thereof.

In a particular embodiment, the at least cosmetic agent of the conjugates of the present invention is selected from the group consisting of an agent capable to trigger tissue repair and/or regeneration, a micelle and a vitamin.

The term "active ingredient capable to trigger tissue repair and/or regeneration", as used herein, refers to regeneration of the skin cells allowing reducing e.g. skin stretch marks on a human skin, or allows healing skin cells after a burn, such as but not limited to a sun burn.

Pharmaceutical, Diagnostic, Theranostic and (Dermo-) cosmetic Compositions

In a further aspect, the invention also relates to a pharmaceutical, diagnostic or theranostic composition comprising at least the conjugate of the present invention comprising at least an active pharmaceutical agent and/or an imaging agent, respectively, and one or more pharmaceutically, diagnostically and theranostically acceptable excipients or carriers, respectively.

As stated above, the present invention also relates to a pharmaceutical composition (or formulations) that comprises at least an active pharmaceutical agent, the cross polymer of the invention (or a pharmaceutically acceptable salt or solvate thereof), and one or more pharmaceutically acceptable excipients. The excipients must be "acceptable" in the sense of being compatible with the remaining ingredients of the composition and not be harmful for those taking said composition.

The nature of the pharmaceutical composition, as is well known, will be dependent on the nature of the active pharmaceutical agent and its administration route. In principle, any administration route may be used, for example, oral, systemically, e.g., by intravenous, subcutaneous or intramuscular injection, intrathecal, intranasal, ocular delivery, rectal, topical and subcutaneous injection.

Solid pharmaceutical formulations for oral administration include tablets, granules and capsules. In any case, the manufacturing method will be based on simple mixing, dry granulation or wet granulation of the active principle with excipients. These excipients may be, for example, diluents such as lactose, microcrystalline cellulose, mannitol or calcium hydrogen phosphate; binding agents such as, for example, starch, gelatine or polyvinylpyrrolidone; disaggregating agents such as sodium carboxymethyl starch or sodium croscarmellose; and lubricating agents such as, for example, magnesium stearate, stearic acid or talc. The tablets may further be coated with adequate excipients by means of known techniques, in order to delay the disaggregation and absorption thereof in the gastrointestinal tract, and thus achieve a sustained action over a longer period of time, or simply improve their organoleptic properties or their stability.

Powders and granules may be obtained in order to prepare oral suspensions by adding water, mixing the active pharmaceutical agent with dispersing or wetting agents, suspending agents and preservatives. Other excipients may also be added, for example, sweetening, flavouring and colouring agents.

Liquid forms for oral administration may include emulsions, solutions, suspensions, syrups and elixirs that contain commonly used inert diluents, such as distilled water, ethanol, sorbitol, glycerol, polyethylene glycols (macrogols) and propylene glycol. Said formulations may also contain adjuvants, such as wetting, suspending, sweetening and flavouring agents, preservatives and pH regulators.

According the present invention, injectable preparations, for parenteral administration, comprise sterile solutions, suspensions or emulsions, in an aqueous or non-aqueous solvent, such as propylene glycol, polyethylene glycol or vegetable oils. These pharmaceutical formulations may also contain adjuvants, such as wetting, emulsifying and dispersing agents, and preservatives. They may be sterilised by means of any commonly known method or prepared as sterile solid formulations that are subsequently dissolved in water or any other sterile injectable medium immediately prior to use. It is also possible to start from sterile raw materials and keep them under these conditions during the entire manufacturing process.

For rectal administration, the pharmaceutical composition of the invention may be preferably suppositories on oily bases, such as, for example, vegetable oils or semi-synthetic solid glycerides, or on hydrophilic bases, such as polyethylene glycols (macrogols).

For nasal administration or inhalation, the pharmaceutical composition of the invention may be in the form of an aerosol, wherefrom it is conveniently released using adequate propellants.

The pharmaceutical compositions of the present invention may also be formulated for topical application, for the treatment of pathologies that affect areas or organs that are accessible by said route, such as the eyes, the skin and the intestinal tract. These pharmaceutical compositions include creams, lotions, gels, powders, solutions and patches wherein the compound is dispersed or dissolved in adequate excipients. Local delivery of growth factors with such a scaffold facilitates wound healing and tissue regeneration in many situations.

The cross polymers of the present invention, either alone or incorporating at least a cosmetic agent, can be also used in (dermo-)cosmetics. Accordingly, the present invention also relates to a (dermo-)cosmetic composition comprising the cross polymer of the present invention or the conjugate of the present invention wherein the at least active agent is a cosmetic agent, and one or more cosmetically acceptable excipient. As such, the (dermo-)cosmetic compositions of the present invention can be widely used in various applications as cleansing compositions, skin care cosmetics, hair cosmetics, and makeup cosmetics. Examples thereof, and without limitation, include milk, cream, mask, fluid, shampoo, body cleanser, facial cleanser, wet tissue (for cleansing), wet tissue (for face cleansing), and makeup remover (for mascara, eye shadow, and foundation). Examples of skin care cosmetics include massage gel, body gel, and face pack. Examples of hair cosmetics include hair treatment, rinse, hair styling preparation, and hair color.

In a particular embodiment, the (dermo-)cosmetic composition is used for the care protection and/or treatment of the skin, the mucous membranes and/or the hair. For reasons linked to comfort when used the (dermo-)cosmetic compositions are intended for topical applications, frequently in the form of emulsion. The (dermo-)cosmetic composition according to the invention may be provided in the form of an oil-in-water (O/W) or water-in-oil (W/O) emulsion. The aqueous phase and the oily phase are, for their part, used in relative proportions that are customary in the cosmetics field, according to the desired galenical form for the (dermo-)cosmetic composition. The determination of these relative proportions is within the competence of those skilled in the art. According to a particularly advantageous characteristic of the invention, the (dermo-)cosmetic composition preferably comprises a physiological moisturizing agent, contained in the aqueous phase, and a physiological emollient agent, contained in the oily phase. When the (dermo-)cosmetic composition is an emulsion, the proportion of the fatty phase ranges from 5 to 80% w/w, preferably from 5 to 50% w/w. The emulsions may or not comprise cosmetically and/or dermatologically acceptable excipients. These excipients may be in particular surfactants, fatty substances, moisturizing agents, preservatives, perfumes, gelling agents, chelators, pigments such as $TiO_2$, etc.

The at least cosmetic agent may be present in the (dermo-)cosmetic composition in the range of 0.001 to 5% weight/weight of the at least cosmetic agent relative to the total weight of the (dermo-)cosmetic composition (w/w), of 0.05 to 4%, of 0.05 to 3%, of 0.04 to 2%, of 0.05 to 2%, or of 0.01 to 1%.

Therapeutic, Diagnostic and Theranostic Uses of the Conjugates of the Invention

The present invention also relates to the use of the conjugate or the pharmaceutical composition of the present invention, wherein the at least active agent is an active pharmaceutical agent, for medicine. Alternatively, the present invention also relates to the conjugate or the pharmaceutical composition of the present invention, wherein the at least active agent is an active pharmaceutical agent, for use in medicine or therapy. Alternatively, the present invention relates to a method for treatment or prevention of a disease which comprises the administration to a subject in need thereof a pharmaceutically effective amount of the conjugate or the pharmaceutical composition of the present invention wherein the at least active agent is an active pharmaceutical agent.

The present invention also relates to the use of the conjugate or the pharmaceutical composition of the present invention wherein the at least active agent is an imaging agent in diagnostics, this can alternatively be worded as a method for the diagnosis of a disease in a subject. Alternatively, the present invention also relates to a conjugate or a diagnostic composition of the present invention wherein the at least active agent is an imaging agent for use in diagnostics.

The present invention also relates to the use of a conjugate or a pharmaceutical composition of the present invention for theranostics. Alternatively, the present invention also relates to a conjugate or a pharmaceutical composition of the present invention for use in theranostics.

Throughout the present description, the term "therapeutic" includes treatment and prevention. The terms "treatment" and "treating", as used herein, refer to the elimination, reduction or decrease of the cause or the effects of a disease. For purposes of this invention, "treatment" and "treating" includes, without being limited thereto, alleviating, reducing or eliminating one or more symptoms of the disease, reducing the grade of the disease, stabilizing (i.e. not worsening) the state of the disease, delaying or slowing the progression of the disease, alleviating or improving the state of the disease, and remission (whether total or partial) of the disease.

As used herein, the terms "prevention", "preventing" and "prevent" refer to the administration of a compound, or a pharmaceutically acceptable salt thereof, or a pharmaceutical composition according to the invention to a subject who has not been diagnosed as possibly having the disease at the time of the administration. Prevention also includes avoiding the reappearance of the disease in a subject who has previously suffered said disease. The prevention may be complete or partial. As used herein, the terms "diagnostic" and "diagnosis" refers to is the identification of the nature and cause of a certain phenomenon.

The term "theranostic", as used herein, refers to diagnostic therapy for individual patients to test them for possible reaction to taking new medication and to tailor a treatment plan for them, in other words, is a form of diagnostic therapy that tests patient's reaction to medication based on the test results.

The terms "subject", "individual", "animal" and "patient" include any subject, particularly a mammalian subject, for whom therapy and/or prevention is desired. Mammalian subjects include humans, domestic animals, farm animals, and zoo or pet animals. In a particular embodiment of the invention, the subject is a mammal. In a more particular embodiment, the subject is a human, preferably a human of any race and sex.

Alternatively, the invention relates to the use of the conjugate or the pharmaceutical composition of the invention and one or more pharmaceutically acceptable excipients or carriers, for the preparation or the manufacture of a medicament.

The present invention also relates to a method of cosmetic skin care comprising delivering topically to the skin of a subject a cosmetically effective amount of the (dermo-) cosmetic composition of the invention. In a particular embodiment, the method of cosmetic skin care is for performing a cosmetic care selected from the group consisting of avoiding or lowering the harmful effects of free radicals on the skin, for slowing down or eliminating rashes or sensations of skin prickling or stinging, of favoring keratinocyte differentiation, of restoring normal moisturizing of the epidermis, of improving skin grain fineness, of slowing down or treating the effects of aging on the skin, of attenuating hyperpigmentation, comprising delivering topically to skin areas of a human being in need thereof, of a cosmetically effective amount of the cosmetic formulation of the present invention.

The expressions "pharmaceutically effective amount" and "cosmetically effective amount", as used herein, is understood as an amount capable of providing a therapeutic effect and a cosmetic effect, respectively, and which can be determined by the person skilled in the art by commonly used means.

Culture Medium and Uses Thereof

Figure 14:
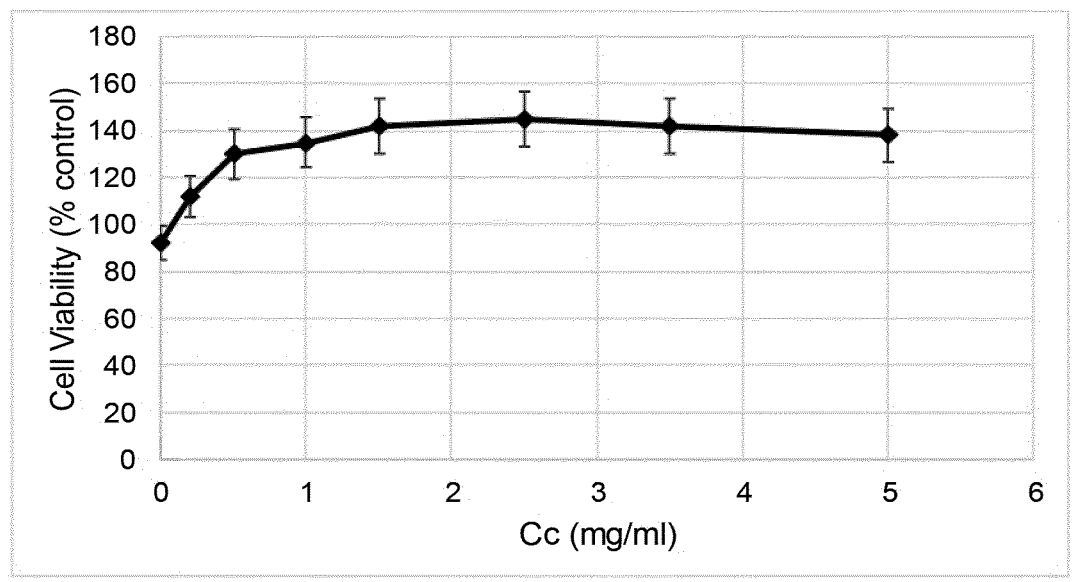
FIG. 14 shows the cell viability of the cross polymer obtained in Example 1a in fibroblasts.

The present invention also relates to a culture medium for cells and/or tissues comprising the cross polymer of the present invention. As well as a method of culturing cells and/or tissues comprising culturing said cells and/or tissues in said culture medium (as shown in FIG. 14). As used herein and in the appended claims, the singular forms "a", "an", and "the" include plural referents unless the context clearly dictates otherwise. For example, "a" or "an" means "at least one" or "one or more". Reference to "the method" includes reference to equivalent steps and methods disclosed herein and/or known to those skilled in the art.

ASPECTS/EMBODIMENTS
HEREIN—PRESENTED IN CLAIM FORMAT

1. A cross-polymer comprising a recurring unit of formula (I) below:

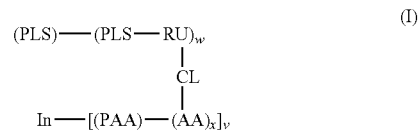

or its salt, solvate or isomer, wherein:
PLS is a radical of a polysaccharide;
PLS-RU is a radical of a repeating unit of the polysaccharide;
PAA is a radical of a polyamino acid, wherein the polyamino acid is selected from the group consisting of a homo-, a random and a block co-polyamino acid, with the proviso that the homo-polyamino acid is not polycationic;
AA is a radical of an amino acid unit of the polyamino acid;
subscript x of the radical (AA) is an integer ranging from 1 to 200;
subscript v of the radical [(PAA)-(AA)$_x$] is an integer ranging from 1 to 48;
subscript w of the radical (PLS-RU) is an integer ranging from 1 to 200;
In is a ROP initiator which comprises a terminal X group per each [(PAA)-(AA)] radical, wherein each terminal X group is directly bond to each [(PAA)-(AA)] radical, and wherein the terminal X group is selected form the group consisting of —NH—, —O—, —S—, or combinations thereof;
CL is a radical selected from the group consisting of: $(C_1-C_{500})$-alkyl, wherein two or more H are substituted by: (1) $(C_1-C_{500})$-alkyl; (2) $(C_3-C_{30})$-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) $N(H)NH_2$, (12) $R_gCOR_h$, (13) $COOR_i$, (14) $CON(R_j)(R_k)$, (15) $R_lN(R_m)CON(R_n)$ $(R'_n)$, (16) $(C_1-C_{30})$-alkene, (17) $(C_1-C_{30})$-alkyne, (18) $N_3$, (19) $R_oCH(OR_p)(OR_q)$, (20) $R_rCH(SR_s)(SR_t)$, (21) $R_uB$ $(OR_v)(OR_w)$, (22) $COR_x$; and wherein none, one of more C, are independently replaced by $(C_3-C_{30})$-cycloalkyl, aryl, aryl-$(C_1-C_{30})$-alkyl, $NR_yR_z$, CO, O, S, S(O), S(O$_2$), B, P and (O—CH$_2$—CH$_2$)$_A$;

subscript A of the radical (O—CH$_2$—CH$_2$) is an integer number between 1 and 500;

$R_a$, $R_b$, $R_c$, $R_d$, $R_e$, $R_f$, $R_h$, $R_i$, $R_j$, $R_k$, $R_m$, $R_n$, $R'_n$, $R_p$, $R_q$, $R_s$, $R_t$, $R_v$, $R_w$, $R_x$, $R_y$ and $R_z$ are radicals independently selected from the group consisting of H, $(C_1-C_{30})$-alkyl, $(C_1-C_{30})$-alkylphenyl, phenyl-$(C_1-C_{30})$-alkyl, and $(C_3-C_8)$-cycloalkyl; wherein, in any of them, except for H, one or more carbons are optionally substituted by a heteroatom selected from the group consisting of O, S, S(O), S(O$_2$), halide, N, NH, P, and CO;

$R_g$, $R_j$, $R_o$, $R_r$ and $R_u$ are radicals independently selected from the group consisting of $(C_1-C_{30})$-alkyl, $(C_1-C_{30})$-alkylphenyl, phenyl-$(C_1-C_{30})$-alkyl, and $(C_3-C_8)$-cycloalkyl; wherein, one or more carbons are optionally substituted by a heteroatom selected from the group consisting of O, S, S(O), S(O$_2$), halide, N, NH, P, and CO;

with the proviso that: (1) CL may be present or not, so that if CL is not present, the PLS-RU radical and the AA radical form a direct stable bond.

2. The cross polymer according to claim 1 wherein the subscript v is an integer between 1 and 5 and each X terminal group is —NH—.

3. The cross polymer according to any of the claims 1-2 wherein CL is not present.

4. The cross polymer according to any of the claims 1-2 wherein CL is present.

5. The cross polymer according to any of the claims 3-4, wherein PAA is a radical of formula (II)

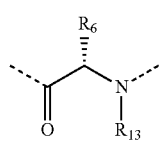

(II)

AA is a radical of formula (III)

(III)

wherein m, n, o, p and q are integers independently selected from 0 to 500, and wherein m+n+o+p+q>1;

$R_1$ to $R_6$ are independently selected from the group consisting of:

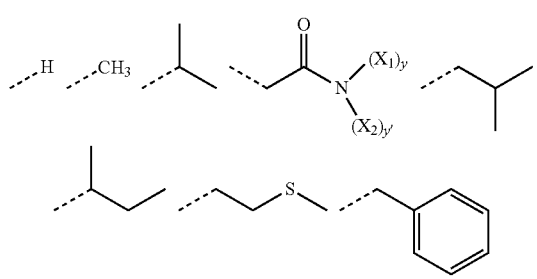

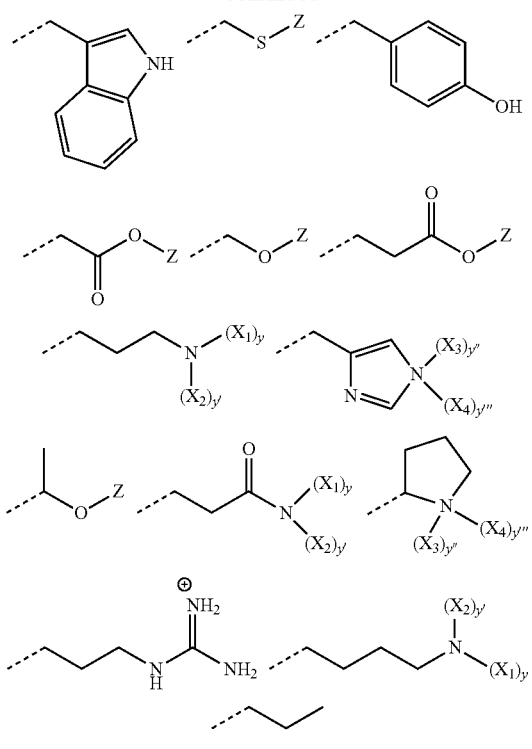

each $X_1$ and $X_2$ is independently selected from the group consisting of H, N, NH$_2$, and Z;

each $X_3$ and $X_4$ is independently selected from the group consisting of H and Z;

each y and y' is an integer independently selected from 0 to 3, wherein y+y'=2 or 3;

each y" and y''' is an integer independently selected from 0 to 2, wherein y"+y'''=1 or 2;

Z is selected from the group consisting of H, metallic counterion and inorganic counterion; and $R_8$ to $R_{13}$ are independently selected from the group consisting of H and —C$_1$C$_4$ alkyl;

with the provisos that: (1) when CL is not present, the AA radical is bound through a peptidic bond to the PAA radical through the terminal amine of the PAA radical; and (2) when CL is present, the AA radical is bound to CL through the amine terminal of the AA radical.

6. The cross polymer according to any of the claims 3-4, wherein

PAA is a radical of formula (IV)

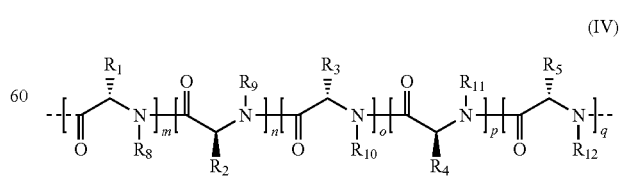

(IV)

AA is a radical of formula (V)

31

(V)

[Chemical structure showing R'₆, R₇, R₁₃ substituents on amino acid backbone]

wherein, m, n, o, p and q are integers independently selected from 0 to 500, and wherein m+n+o+p+q>1;

$R_1$ to $R_5$ are independently selected from the group consisting of:

[Chemical structures shown: H, CH₃, various alkyl groups, acetamide with (X₁)y and (X₂)y', isobutyl, isobutyl variant, methylthioethyl, benzyl, indolylmethyl (tryptophan-like), thioether with Z, hydroxyphenyl (tyrosine-like), carboxylate ester with Z, ether-Z, propanoate-Z, aminoalkyl with (X₁)y and (X₂)y', imidazolyl with (X₃)y'' and (X₄)y''', ether-O-Z, propanamide with (X₁)y, (X₂)y', pyrrolidinyl with (X₃)y'' and (X₄)y''', guanidinium with NH₂ groups, aminobutyl with (X₁)y and (X₂)y']

$R'_6$ is selected from the group consisting of:

[Chemical structures: ether-O, acetyl, propanone, isopropyl ether-O, thioether-S, aminopropyl with (X₁)y, aminobutyl with (X₁)y]

32

-continued

[Chemical structure: pyrrolidinyl with (X₃)y']

each $X_1$ and $X_2$ is independently selected from the group consisting of H, N, $NH_2$, and Z;
each $X_3$ and $X_4$ is independently selected from the group consisting of H and Z;
each subscript y and y' of $R_1$ to $R_5$ is an integer independently selected from 0 to 3, wherein y+y'=2 or 3;
each subscript y" and y''' of $R_1$ to $R_5$ is an integer independently selected from 0 to 2, wherein y"+y'''=1 or 2;
each subscript y of $R'_6$ is 1 or 2;
subscript y' of $R'_6$ is 0 or 1;
each Z is independently selected from the group consisting of H, metallic counterion and inorganic counterion;
$R_7$ is a radical selected from the group consisting of: $(C_1-C_{500})$-alkyl, wherein one or more H are substituted by: (1) $(C_1-C_{500})$-alkyl; (2) $(C_3-C_{30})$-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) $N(H)NH_2$, (12) $R_gCOR_h$, (13) $COOR_i$, (14) $CON(R_j)(R_k)$, (15) $R_lN(R_m)CON(R_n)$ ($R'_n$), (16) $(C_1-C_{30})$-alkene, (17) $(C_1-C_{30})$-alkyne, (18) $N_3$, (19) $R_oCH(OR_p)(OR_q)$, (20) $R_rCH(SR_s)(SR_t)$, (21) $R_uB(OR_v)(OR_w)$, (22) $COR_x$; and wherein none, one of more C, are independently replaced by $(C_3-C_{30})$-cycloalkyl, aryl, aryl-$(C_1-C_{30})$-alkyl, $NR_yR_z$, CO, O, S, S(O), $S(O_2)$, B, P and $(O-CH_2-CH_2)_A$;
subscript A of the radical (O—CH₂—CH₂) is an integer number between 1 and 500;
$R_a, R_b, R_c, R_d, R_e, R_f, R_h, R_i, R_j, R_k, R_m, R_n, R'_n, R_p, R_q, R_s, R_t, R_v, R_w, R_x, R_y$ and $R_z$ are radicals independently selected from the group consisting of H, $(C_1-C_{30})$-alkyl, $(C_1-C_{30})$-alkylphenyl, phenyl $(C_1-C_{30})$-alkyl and $(C_3-C_8)$-cycloalkyl; wherein in any of them, except for H, one or more carbons are optionally substituted by a heteroatom selected from the group consisting of O, S, S(O), $S(O_2)$, halide, N, NH, P, and CO;
$R_g, R_l, R_o, R_r$ and $R_u$ are radicals independently selected from the group consisting of $(C_1-C_{30})$-alkyl, $(C_1-C_{30})$-alkylphenyl, phenyl, $(C_1-C_{30})$-alkyl, and $(C_3-C_8)$-cycloalkyl; wherein, one or more carbons are optionally substituted by a heteroatom selected from the group consisting of O, S, S(O), $S(O_2)$, halide, N, NH, P, and CO; and
$R_8$ to $R_{13}$ are independently selected from the group consisting of H and $(C_1-C_4)$-alkyl;
with the provisos that: (1) when CL is not present, the AA radical is bound through a peptidic bond to the PAA radical through the terminal amine of the PAA radical; and (2) when CL is present, the radical AA is bound to CL through $R'_6$.

7. The cross polymer according to claim 5 wherein $R_1=R_2=R_3=R_4=R_5=R_6$.

8. The cross polymer according to claim 7 wherein said $R_1=R_2=R_3=R_5=R_6$ is selected form the group consisting of:

[Chemical structures: carboxylate-O-Z, thioether-S-Z, isopropyl ether-O-Z]

-continued

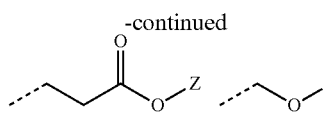

wherein Z is defined as in claim 5.

9. The cross polymer according to claim 6 wherein $R_1=R_2=R_3=R_4=R_5$ and $R'_6$ is the corresponding double radical of said $R_1=R_2=R_3=R_4=R_5$.

10. The cross polymer according to claim 9 wherein said $R_1=R_2=R_3=R_4=R_5$ is selected from the group consisting of:

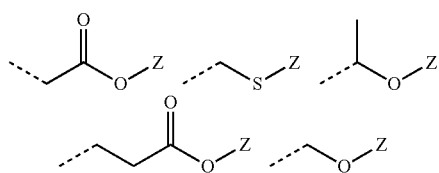

$R'_6$ is selected from the group consisting of:

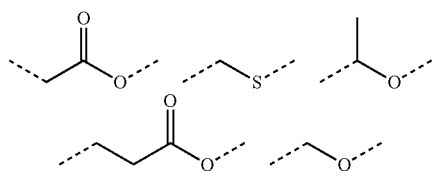

and Z is defined as in claim 6.

11. The cross polymer according to claim 5 wherein the polyamino acid is a random or block co-polyamino acid.

12. The cross polymer according to claim 11 wherein $R_1$, $R_2$, $R_3$, $R_4$, $R_5$ and $R_6$ are independently selected from the group consisting of:

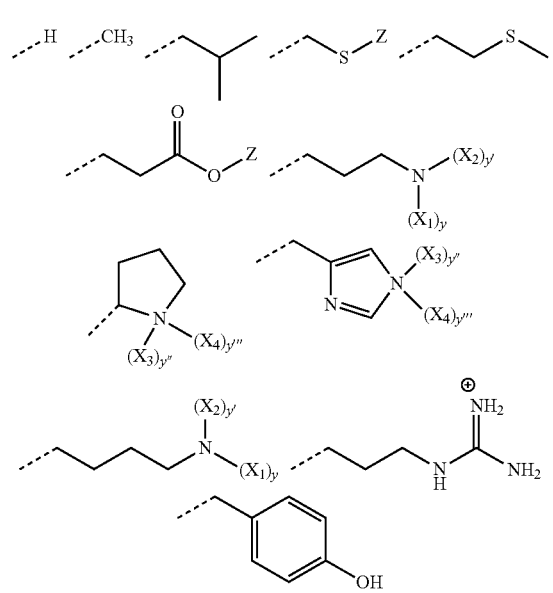

Z, $X_1$ to $X_4$, y, y', y" and y'" are as defined in claim 5.

13. The cross polymer according to claim 12 wherein $R_1$, $R_2$, $R_3$, $R_4$, $R_5$ and $R_6$ are independently selected from the group consisting of:

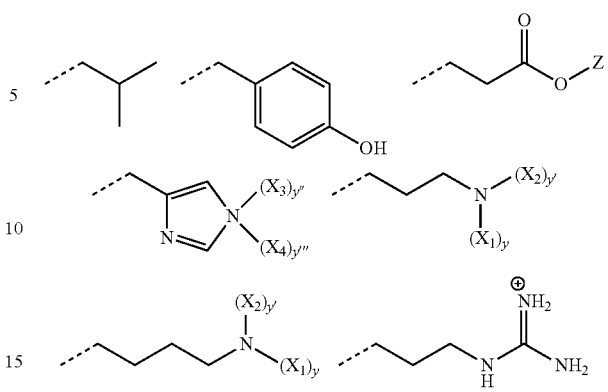

Z, $X_1$ to $X_4$, y, y', y" and y'" are as defined in claim 5.

14. The cross polymer according to claim 6 wherein the polyamino acid is a random or blok co-polyamino acid.

15. The cross polymer according to claim 14 wherein $R_1$ to $R_5$ are independently selected from the group consisting of:

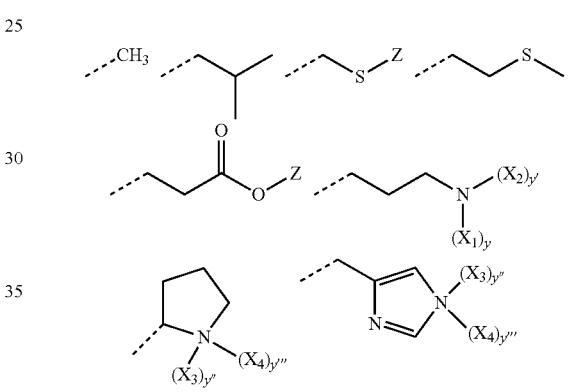

$R'_6$ is selected from the group consisting of:

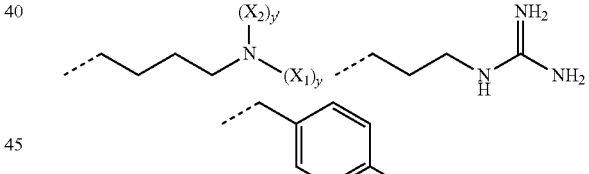

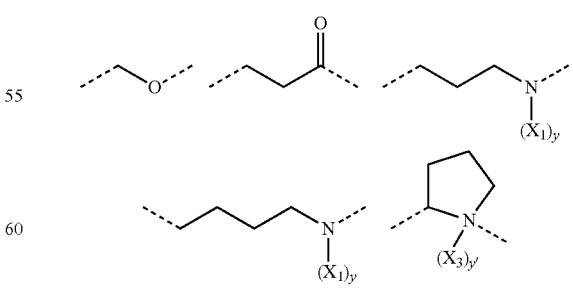

and Z, $X_1$ to $X_4$, y, y', y" and y'" are as defined in claim 6.

16. The cross polymer according to claim 15 wherein $R_1$ to $R_5$ are independently selected from the group consisting of:

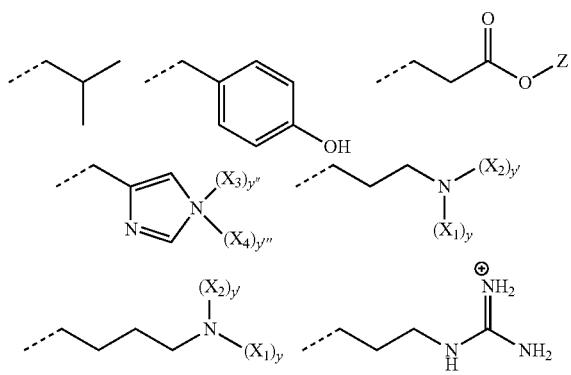

and Z, $X_1$ to $X_4$, y, y', y" and y''' are as defined in claim 6.

17. The cross polymer according to any of the claims 6, 9, 10 and 14-16 wherein $R_7$ is selected from the group consisting of H, CO—$(C_1$-$C_{20})$-alkyl, CONH—$(C_1$-$C_{20})$-alkyl and pyroglutamate.

18. The cross polymer according to any of the claims 4-17 wherein CL is selected form the group consisting of:

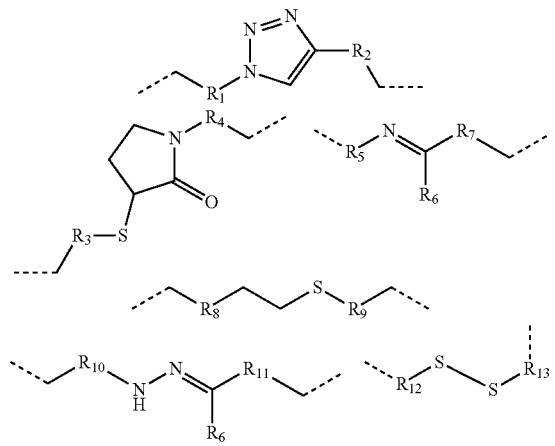

wherein $R_1$ to $R_5$ and $R_7$ to $R_{13}$ are independently selected from the group consisting of:

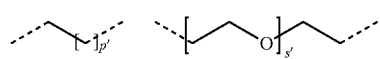

p' and s' are integers independently selected from 0 to 500; and $R_6$ is independently selected from the group consisting of H and $(C_1$-$C_4)$-alkyl.

19. The cross polymer according to any of the claims 4-17 wherein CL is —NH—CH(COOH)—$(C_1$-$C_{30})$-alkyl-NH—.

20. The cross polymer according to any of the claims 1 to 19 wherein PLS is a polysaccharide selected from the group consisting of hyaluronic acid, pectin, chitosan and chondroitin sulfate.

21. The cross polymer according to claim 3 wherein the polysaccharide is hyaluronic acid, PAA is polyglutamate, AA is glutamate, v is an integer between 2 and 4 and x+w is an integer between 2 and 200.

22. The cross polymer according to claim 4 wherein the polysaccharide is hyaluronic acid, PAA is polyglutamate, AA is glutamate, v=1, x+w is an integer between 2 and 200 and CL is —NH—CH(COOH)—$(C_1$-$C_4)$-alkyl-NH—.

23. A conjugate comprising the cross polymer as defined in any of the claims 1 to 22 and at least an active agent which is bound to the cross polymer.

24. The conjugate according to claim 23 wherein the at least active agent is bound to the cross polymer through the PLS-(PLS-RU)$_w$ radical and/or the (PAA)-(AA)$_x$ radical.

25. The conjugate according to any of the claims 23-24 wherein the at least active agent is selected from the group consisting of an active pharmaceutical agent, an imaging agent, and combinations thereof.

26. The conjugate according to claim 25 wherein the at least active pharmaceutical agent is selected from the group consisting of vaccines, antioxidants, anti-inflammatories, neuroprotective, vitamins, UV-filters, ions, metals, growth factors, stem cells, natural extracts, chemotherapeutics, Rho-associated protein kinase (ROCK) inhibitors, proteins, antidotes, analgesics, anesthetics, antidiabetics, antibiotics, antifungals, antihistamines, corticoids, anticancer agents, anti-metastatic agents, anti-apoptotics, pro-apoptotics, neuroprotective agents, immunostimulant agents and immunosupressor agents.

27. Use of the conjugate as defined in claim 25 as an imaging agent.

28. The conjugate according to any of the claims 23-24 wherein the at least active agent is a cosmetic agent.

29. The conjugate according to claim 28 wherein the at least cosmetic agent is selected from the group consisting of an agent capable to trigger tissue repair and/or regeneration, a micelle and a vitamin.

30. A pharmaceutical, diagnostic or theranostic composition comprising at least a conjugate as defined in any of the claims 25-26, and one or more pharmaceutically, diagnostically and theranostically acceptable excipients or carriers, respectively.

31. A conjugate as defined in any of the claims 25-26 or a pharmaceutical composition as defined in claim 30 for use in medicine or therapy.

32. A conjugate as defined in claim 25 or a diagnostic composition as defined in claim 30 for use in diagnostics.

33. A (dermo-)cosmetic composition comprising a cross polymer as defined in any of the claims 1-22 or a conjugate as defined in any of claims 28-29, and one or more cosmetically acceptable excipient.

34. A culture medium for cells and/or tissues comprising the cross polymer as defined in any of the claims 1-22.

35. A method of culturing cells and/or tissues comprising culturing said cells and/or tissues in the culture medium as defined in claim 34.

EXAMPLES

Chemicals

All chemicals used in the following examples were of reagent grade and used without further purification and were purchased from Sigma-Aldrich unless otherwise stated.

Hyaluronic acids of different MW (molecular weight) were purchased from Saequim Especiali-dades S. L. (Aurora, 50 KDa), when used for the chemical reactions detailed in the Examples, and from Soliance (PrimalHyal300, 200 KDa), when used for comparison purposes in the Examples. Hyaluronidase (HAase) of 999 units/mg and 4-(4,6-Dimethoxy-1,3,5-triazin-2-yl)-4-methylmorpholinium chloride (DMTMMCl) were purchased from Sigma Aldrich. Anhydrous N, N-Dimethylformamide (DMF, ≥99.8% anhydrous), dimethyl sulfoxide (DMSO, ≥99.8% anhydrous) and tetrahydrofuran (THF, ≥99.8% anhydrous) were purchased from Scharlab S. L. (Sentmenat, Spain). Sodium nitrate, sodium hydroxide, sodium phosphate monobasic and di-sodium hydrogen phosphate heptahydrate were obtained from VWR International. L-lysine hydrochloride salt and concentrated hydrochloride acid 12M were obtained from Fisher Scientific. Cyanine 5.5 amine and DiL dyes were purchased from Lumiprobe and Invitrogen, respectively. Deuterium oxide was purchased from Deutero GmbH. Ultrapure water with resistivity of 18MΩ·cm was used in all aqueous preparations (Milli-Q® ultrapure). Sodium polyglutamate of 15 KDa initiated with n-butylamine, and sodium polyglutamate of 3 KDa of different architectures, namely, initiated with n-butylamine or 1,4-n-butyldiamine, were synthesized as described elsewhere (see for instance, DENG, C. et al., 2014; LU, H. et al., 2014). Tangential Flow Filtration (TFF) model equipment 900-1893 with a 30 KDa MWCO (Molecular Weight Cut Off) PES column was provided form Spectrum Labs. Vi-vaspin 100 KDa MWCO PES was purchased from Sartorius.

$^1$H NMR Spectroscopy $^1$H NMR spectra were recorded at 27° C. (300° K) on a 300 Ultrashield™ from Bruker (Billerica Mass., USA). Data were processed with the software Topspin (Bruker GmbH, Karlsruhe, Germany). Samples were prepared at 5 mg/mL in deuterated solvents.

SEC-RI-MALS

SEC measurements in aqueous media containing 0.1M of $NaNO_3$ and 0.005% (w/w) azide as an additive were performed in an AF2000 system from Postnova Analytics (Landsberg, Germany). The system was configured to work on SEC mode with an isocratic pump (PN1130), an autosampler (PN5300), a refractive index (RI, PN3150), and 21 angle-multi angle light scattering (MALS, PN3621). A working flow rate of 0.7 mL/min at 30° C. was employed with one TSKgel G6000PWXL column. Refractive index and Multi Angle Light Scattering were used for detection and MW determination, calibration of both RI and MALS detectors was achieved with well-defined Pullulan (50 KDa) and validation with polymethacrylic acid sodium salt (62.5 KDa PMASS) standards, purchased from Polymer Standards Service (PSS)/Mainz Germany. For characterization of NaPGA/Na-nBu(PGA)$_2$, NaHA and cross-polymers, 30 µL of the corresponding solution of 5 mg/mL were injected each time. dn/dc values were determined from recovered mass assuming 95-100% recovery from the chromatographic column and found to be within 0.185-0.195 for PGA, and 1.4-1.5 for HA and cross-polymers.

Example 1. Design and Synthesis of Hyaluronic Acid-poly-L-glutamic Acid-L-lysine-([HA]-[PGA]-[Lys]) Cross Polymers Two different [HA]-[PGA] representative cross-polymers were synthetized using L-lysine as the linker molecule following conventional peptide coupling procedures known to the person skilled in the art (e.g. BARZ, M et al., 2013). The synthetic method provided a procedure for controlling the cross-linking degree and the enrichment of cross-polymer within the complex product mixture, by carefully controlling the reaction conditions (e.g. molar ratio of reagents, pH, reaction mixture concentration, etc.).

General Synthetic Procedure

The following solutions were prepared:

Sodium hyaluronate (NaHA) was dissolved in distilled water (solution A)

Sodium poly-L-glutamate initiated with n-butylamine (Na-nBuPGA) was dissolved in distilled water (solution B)

4-(4,6-Dimethoxy-1,3,5-triazin-2-yl)-4-methylmorpholinium chloride (DMTMMCl) was dissolved in distilled water (solution C)

L-lysine hydrochloride salt (Lys.HCl) was dissolved in distilled water (solution D)

Solutions A and B were first mixed. Solution C was then added. The resulting reaction mixture was stirred for 15 minutes. Afterwards, solution D was added, and the reaction was carried out over night at RT (room temperature), the pH was then adjusted. The product obtained was purified by dialysis using a Tangential Flow Filtration (TFF) system with a membrane of MWCO 30 KDa washing with phosphate buffer (PB) 5 mM at pH 7.5 and with distilled water sequentially. The solution was lyophilized and a white powder was obtained. FIG. 1 shows the $^1$H NMR spectra of the raw materials (L-lysine hydrochloride salt Lys.HCl, sodium poly-L-glutamate NaPGA and sodium hyaluronate NaHA) used to prepare the above solutions.

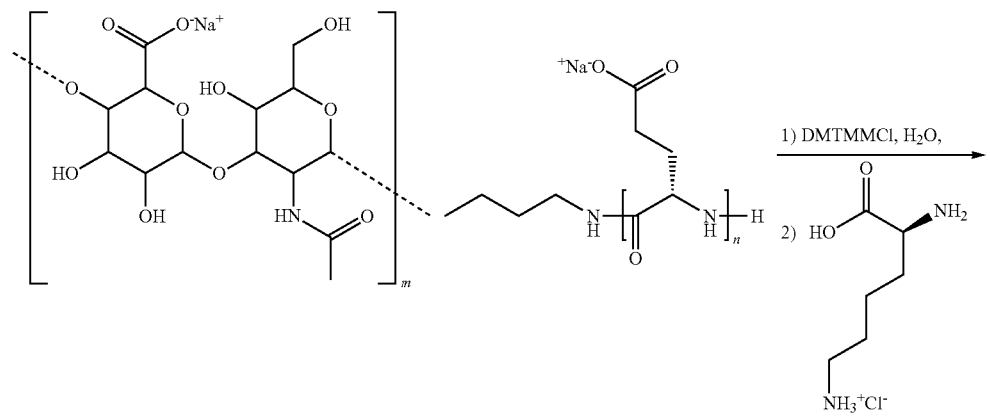

Scheme 1. Synthetic methodology for the synthesis of [HA]-[PGA]-[Lys] cross polymer of Examples 1a and 1b, wherein m is 126, n is 100, and x + y ≤ 6.4.

-continued

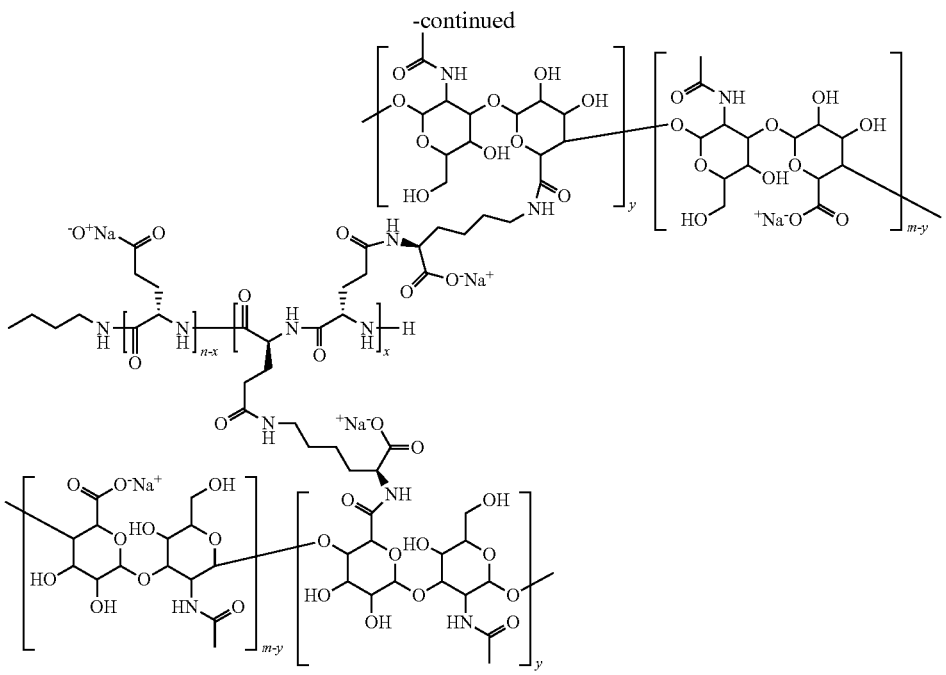

Example 1a. Low Cross-linking Degree [HA]-[PGA]-[Lys] Cross Polymer

A low cross-linking degree [HA]-[PGA]-[Lys] cross polymer was synthetized following the previously described general synthetic procedure. The amounts of the reagents employed in each reaction are detailed in Table 1 below. The total volume of reaction was 1.165 mL. The reactions were performed at pH=6-7.

TABLE 1

| Compound | NaHA | Na-nBuPGA | Total carboxylates | Lys•HCl | DMTMMCl |
|---|---|---|---|---|---|
| MW monomer (Da) | 401.31 | 151.11 | — | 182.65 | 276.72 |
| mol | 1.74E−01 | 1,22E−02 | 1.87E−01 | 5.58E−03 | 8.72E−02 |
| grams | 70.00 | 1.8451 | — | 1.0195 | 24.1340 |
| equivalents | 1 | 0.07 | 1.07 | 0.032 | 0.5 |

FIG. 1 shows the $^1$H NMR spectra of the synthesized [HA]-[PGA]-[Lys] cross polymer obtained in Example 1a after purification by elimination of the side residues. As shown in the $^1$H NMR spectra, the PGA residues were incorporated within the structure of the resulting cross polymer (see dashed region).

Figure 2:
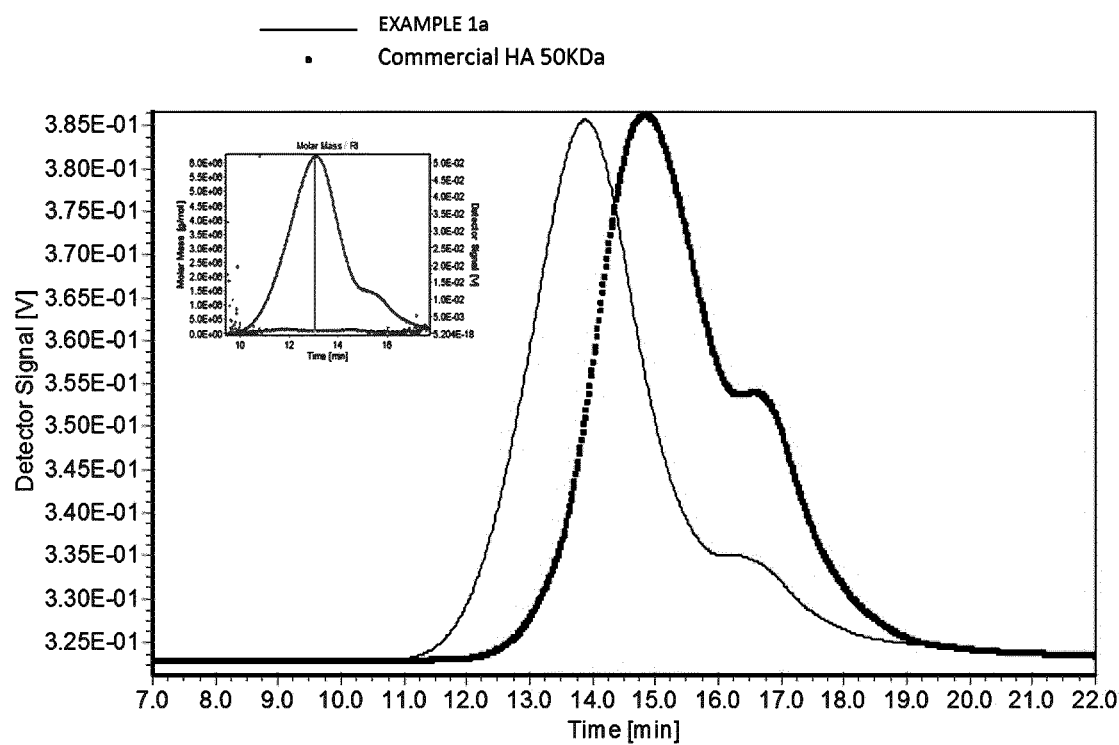
Figure 3:
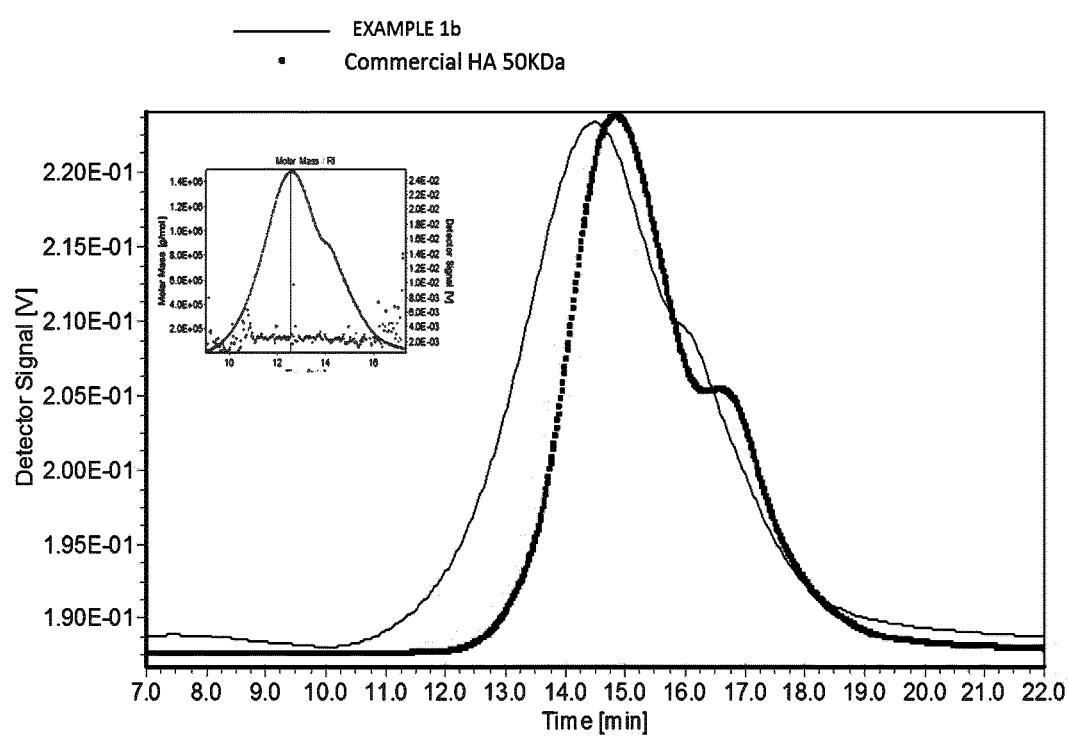
FIG. 3 shows the size-exclusion chromatography analysis of [HA]-[PGA]-[Lys] cross polymer obtained in Example 1b.

Chromatograms for the commercial NaHA before (solid line) and after cross-linking with NaPGA (dash line) were obtained using an RI detector. As shown in FIG. 2, the inset shows the overlapping of RI signal and MW distribution after determination of absolute MW (refractive index and light scattering). Table 2 below shows the quantitative analysis of MW and PDI (polydispersity index) via RI-MALS analysis of NaHA and the cross polymer obtained in Example 1a. The cross-linking was evidenced by the two-fold increase in MW of [HA]-[PGA]-[Lys] cross polymer obtained in Example 1a vs NaHA.

TABLE 2

| Compound | MW (KDa) | PDI |
|---|---|---|
| NaHA | 50.4 | 1.37 |
| [HA]-[PGA]-[Lys] cross polymer | 101.4 | 1.68 |

Example 1b. High Cross-linking Degree [HA]-[PGA]-[Lys] Cross Polymer

A high cross-linking degree [HA]-[PGA]-[Lys] cross polymer was synthetized following the previously described general synthetic procedure. The amounts of the reagents employed in each reaction are detailed in Table 1 above, but the total volume of reaction was 840 mL. The reaction was performed at pH=8.5.

As shown in the $^1$H NMR spectra of the synthesized [HA]-[PGA]-[Lys] cross polymer obtained in Example 1b of FIG. 1, the PGA residues were incorporated within the structure of the synthetized cross polymer (see dashed region).

Chromatograms for the commercial NaHA before (solid line) and after cross-linking with the NaP-GA residues (dash line) were obtained using an RI detector. As shown in FIG. 2, the inset shows the overlapping of RI signal and Mw distribution after determination of absolute MW (refractive index and light scattering). Table 3 below shows the quantitative analysis of MW and PDI via RI-MALS analysis of NaHA and the cross polymer obtained in Example 1b. The

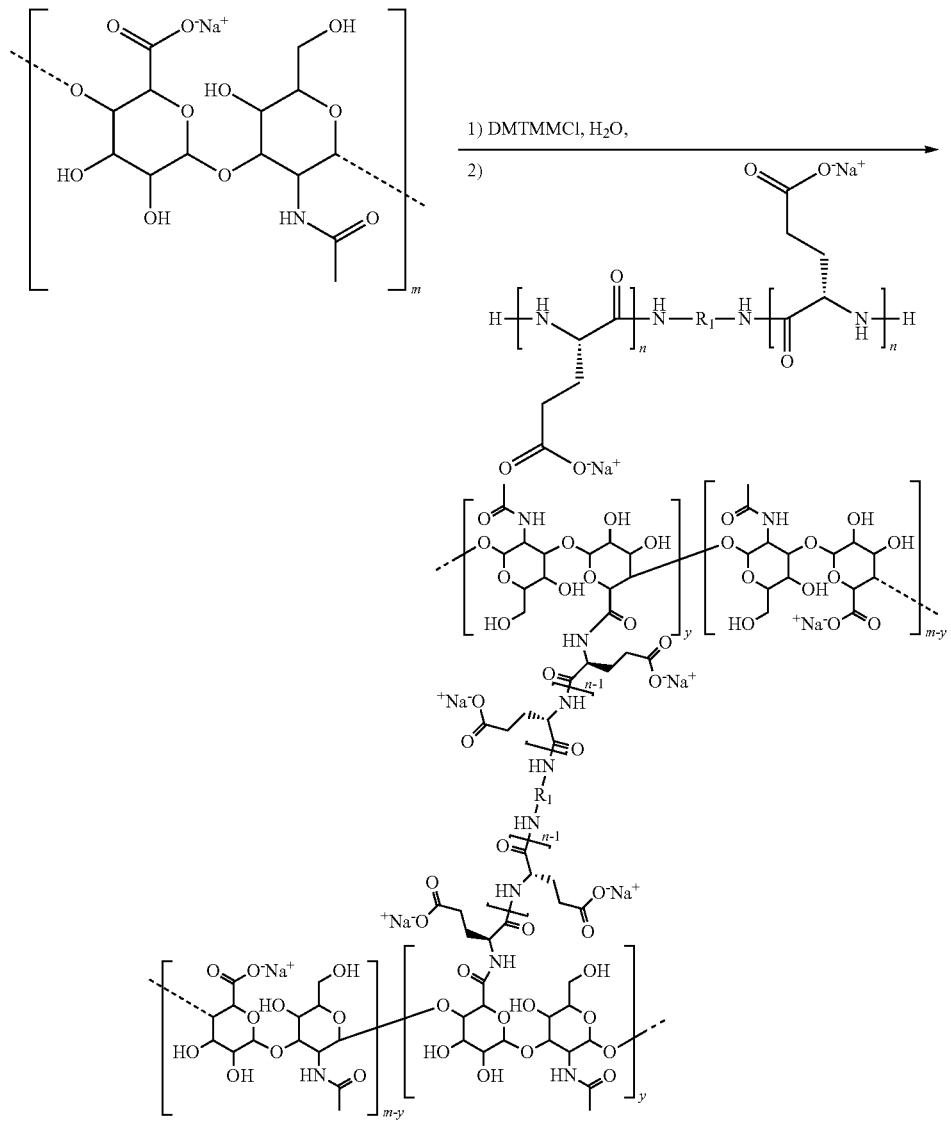

crosslinking was evidenced by the three-fold increase in MW of [HA]-[PGA]-[Lys] cross polymer obtained in Example 1b vs NaHA.

TABLE 3

| Compound | Mw (KDa) | PDI |
| --- | --- | --- |
| NaHA | 50.4 | 1.37 |
| [HA]-[PGA]-[Lys] cross polymer | 145.7 | 1.37 |

Example 2. Design and Synthesis of Self-cross-linking Hyaluronic Acid-poly-L-glutamic Acid ([HA]-[PGA]) Cross Polymer A representative [HA]-[PGA] cross polymer was synthetized using a bifunctional and symmetric PGA motif having two N-terminus reactive amine moieties, and following conventional synthetic procedures described elsewhere.

Synthetic methodology for the synthesis of [HA]-[PGA] cross polymer using a bifunctional poly-L-glutamate, namely a PGA initiated with the bifunctional n-butyl diamine (Na-nBu(PGA)$_2$), wherein m is 126, n is 100 and ≤6.

General Synthetic Procedure

For the synthesis of the self-cross-linking [HA]-[PGA] cross polymer, using the bifunctional and symmetric PGA motif having two N-terminus reactive amine moieties, the following solutions were prepared:

Sodium hyaluronate (NaHA) was dissolved in distilled water (solution A)

4-(4,6-Dimethoxy-1,3,5-triazin-2-yl)-4-methylmorpholinium chloride (DMTMMCl) was dissolved in distilled water (solution B)

Bifunctional sodium poly-L-glutamate, initiated with 1,4-butyldiamine (Na-nBu(PGA)$_2$), was dissolved in distilled water (solution C)

The amounts employed of the above solutions are summarized in Table 4 below.

TABLE 4

| Compound | NaHA | Na-nBu(PGA)$_2$ | DMTMMCl |
|---|---|---|---|
| MW (Da) | 401.32 | 3020 | 276.72 |
| mol | 1.25E-03 | 3.74E-05 | 6.23E-04 |
| grams | 0.5000 | 0.1129 | 0.1724 |
| equivalents | 1 | 0.03 | 0.50 |

Figure 4:
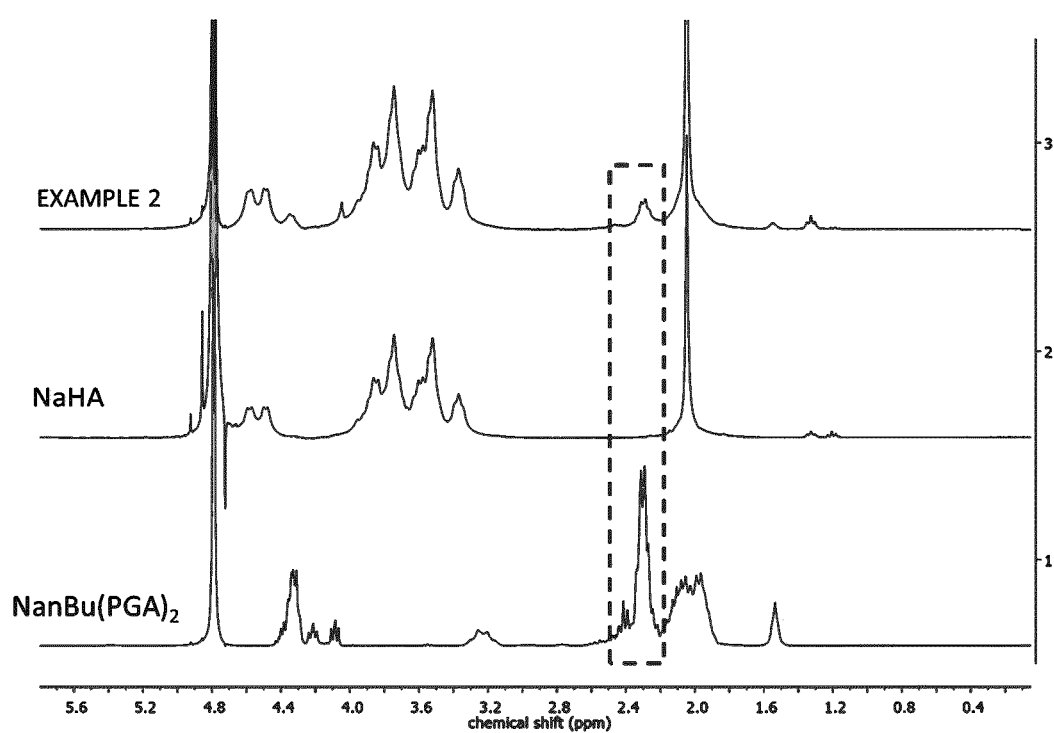
FIG. 4 shows the $^1$H NMR spectra of the raw materials (bifunctional sodium poly-L-glutamate initiated with n-butyldiamine (Na-nBu(PGA)$_2$) and sodium hyaluronate (NaHA), and the synthesized [HA]-[PGA] cross polymer obtained in Example 2.

Solution B was added over A, and the pH was adjusted to 7 with NaOH. The resulting reaction mixture was stirred for 15 minutes. Afterwards, solution C was added, and the reaction was carried out over night at RT. The pH was adjusted to 8.5, and it was measured to be 6-5. The product obtained was purified by dialysis using a Tangential Flow Filtration (TFF) system with a membrane of MWCO 30 KDa washing with PB 5 mM at pH 7.5 and with distilled water sequentially. The solution was lyophilized and a white powder was obtained. FIG. 4 shows the $^1$H NMR spectra of the raw materials, sodium poly-L-glutamate (Na-nBu-(PGA)$_2$) and sodium hyaluronate (NaHA) used to prepare the above solutions, used to prepare the above solutions. As shown in the spectra, the PGA residues were incorporated within the structure of the synthetized cross polymer (see dashed region).

For the synthesis of the [HA]-[PGA] cross polymer using the monofunctional PGA motif having a single N-terminus reactive amine moiety, the following solutions were prepared (the amounts employed of the solutions are also those summarized in Table 4 above):

Sodium hyaluronate (NaHA) was dissolved in distilled water (solution A)

4-(4,6-Dimethoxy-1,3,5-triazin-2-yl)-4-methylmorpholinium chloride (DMTMMCl) was dissolved in distilled water (solution B)

Monofunctional sodium poly-L-glutamate (Na-nBuPGA) initiated with n-butylamine was dissolved in distilled water (solution C)

Solution B was added into A, and the pH was adjusted to 7 with a few microliters of NaOH 1M. The resulting reaction mixture was stirred for 15 minutes. After that, solution C was added and the pH was adjusted to 8.5 with a few microliters of NaOH 1M. The reaction was carried out over night at RT. Then, the product was purified by dialysis using a Tangential Flow Filtration (TFF) system with a membrane of MWCO 30 KDa washing with PB 5 mM at pH 7.5 first and the with distilled water. The solution was lyophilized and a white powder was obtained.

Figure 5:
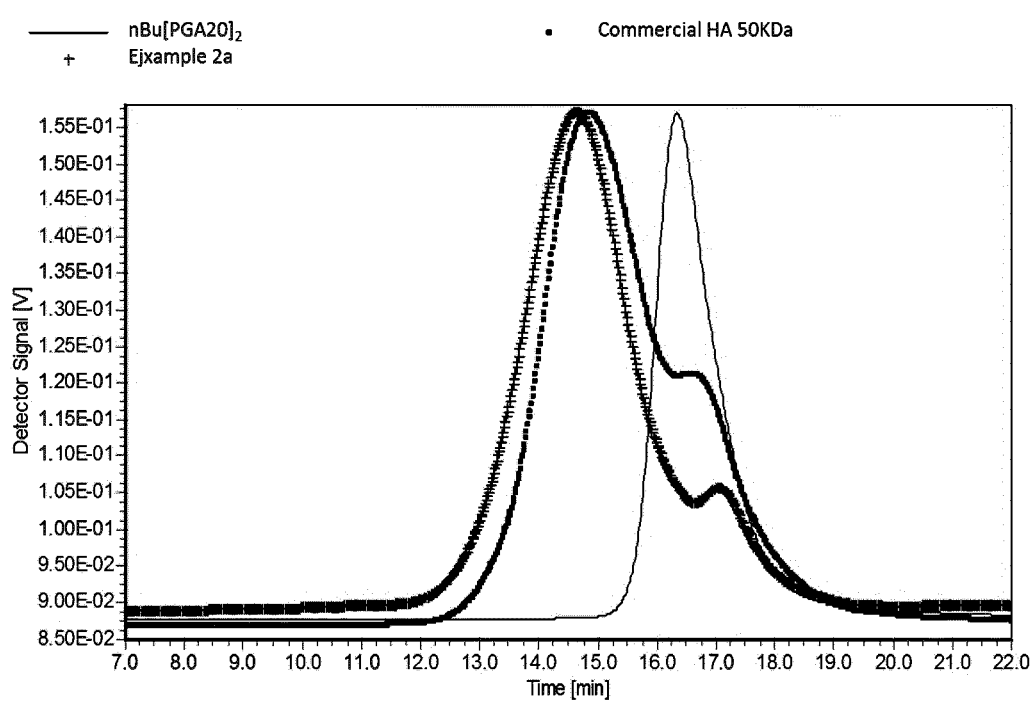
FIG. 5 shows the size-exclusion chromatography analysis of self-cross-linking [HA]-[PGA] cross polymer obtained in Example 2 using Na-nBu(PGA)$_2$.

To check that the bifunctional PGA was effectively cross-linking the HA through the two end amine moieties, size-exclusion chromatography analysis of the corresponding self-crosslinking [HA]-[PGA] cross polymer using the bifunctional and symmetric PGA was obtained (see FIG. 5, solid line). Comparative chromatograms using RI detector were also obtained for the NaHA before (squares line) and after cross-linking with PGA (cross line). The inset shows the overlapping of RI signal and MW distribution after determination of absolute MW (refractive index and light scattering). The cross-linking with bifunctional PGA is evidenced by the two-fold increase in MW. Table 5 below shows the quantitative analysis of MWw and PDI via RI-MALS analysis of Na-nBu(PGA)$_2$, HA and the resulting [HA]-[PGA] cross polymer.

TABLE 5

| Compound | MW (KDa) | PDI |
|---|---|---|
| NaHA | 50.4 | 1.37 |
| Na-nBu(PGA)$_2$ | 4.9 | 1.12 |
| [HA]-[PGA] cross polymer | 110.7 | 1.36 |

Figure 6:
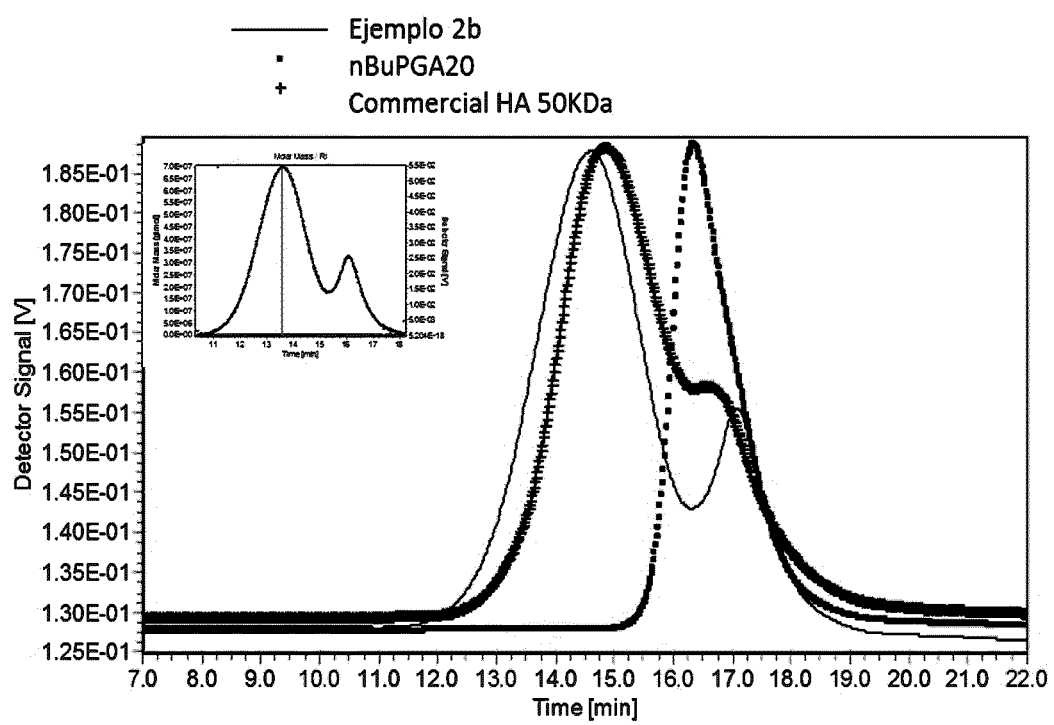
FIG. 6 shows the size-exclusion chromatography analysis of self-cross-linking [HA]-[PGA] cross polymer obtained in Example 2 using Na-nBuPGA.

As a control experiment, monofunctional PGA was employed in the cross-linking reaction. Size-exclusion chromatography analysis of the corresponding self-crosslinking [HA]-[PGA] cross polymer was obtained (see FIG. 6, solid line). Comparative chromatograms using RI detector for the commercial sodium hyaluronate (cross line) and after cross-linking reaction with the monofunctional PGA (solid line). The inset shows the overlapping of RI signal and MW distribution after determination of absolute MW (refractive index and light scattering). The lack of crosslinking is evidenced by the small increase in MW and a higher bimodal nature of chromatogram. Unlike the bifunctional PGA, this monofunctional PGA lacked the capacity to generate cross-linking points, and therefore the results matched with the presence of HA-PGA conjugates rather than cross-linked structures. Table 6 below shows the quantitative analysis of MW and PDI via RI-MALS analysis of NaHA, Na-nBuPGA, and the resulting self-crosslinking [HA]-[PGA] cross polymer which showed a small increase in MW in comparison to parent HA, confirming the formation of HA-PGA conjugates rather than cross polymers.

TABLE 6

| Compound | MW (KDa) | PDI |
|---|---|---|
| NaHA | 50.4 | 1.37 |
| Na-nBuPGA | 2.7 | 1.17 |
| Self-cross-linking [HA]-[PGA] cross polymer | 65.5 | 1.13 |

Example 4. Rheology

Figure 7:
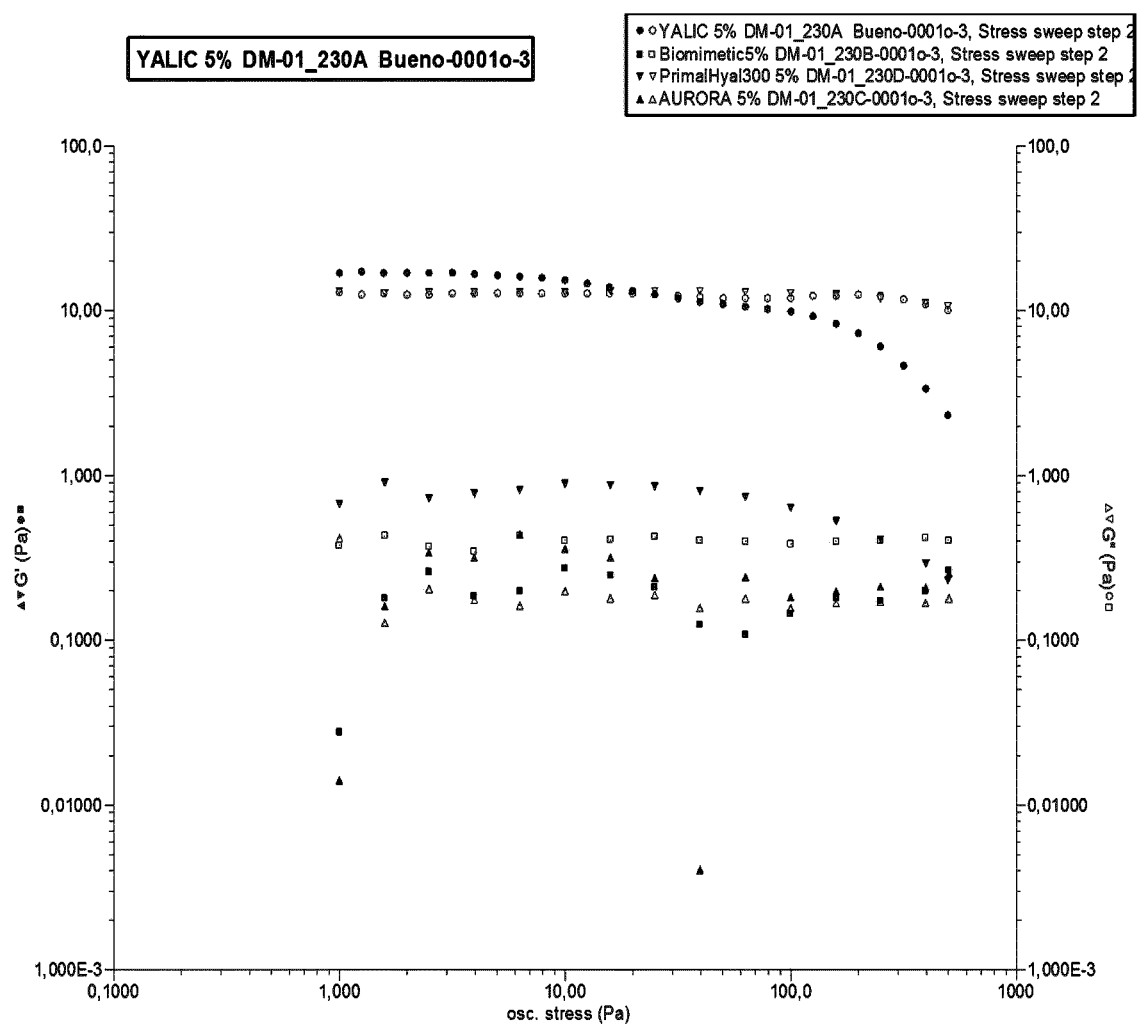
FIG. 7 shows the oscillatory rheological analysis performed with the [HA]-[PGA]-[Lys] cross polymers obtained in Examples 1a (circles) and 1b (squares) and commercial NaHA of 250 KDa (downside triangles) and 50 KDa (upside triangles) at 5% wt. Storage modulus (G', filled symbols) and loss modulus (G", empty symbols) data under oscillatory stress experiment were measured within the linear viscoelastic regime at a frequency of 1 Hz.

Rheological measurements were carried out on a TA AR-G2 rheometer equipped with a Peltier temperature-control accessory, by using a steel parallel plate-plate geometry (40 mm diameter). The gap distance was fixed at 1,000 nm. The tested samples consisted in the cross polymers of Examples 1a, 1b and commercial NaHA (50 KDa and 250 KDa). The samples were prepared under the required conditions in milliQ water and aged for 24 h. A homogeneous layer of sample was placed between the two plates. Frequency and stress sweep steps were performed at 20° C. Viscoelastic properties were studied under oscillatory experiments and results are shown in FIG. 7. All the measurements were carried out within the linear viscoelastic regime (LVR) at a frequency of 1 Hz. For this purpose, the experimental conditions to achieve the LVR were determined by running a stress sweep step (oscillatory stress: 0.1-1,000 Pa at 1 Hz) and a frequency sweep step (0.1-100 Hz at 0.2 Pa). The storage and loss modulus independence with frequency and oscillatory stress applied defined the LVR. Results showed that at the concentration studied (5% wt) only the hydrogel from Example 1 b showed the expected rheological behavior for viscoelastic hydrogels, namely, a storage modulus (G') higher than the loss modulus (G"). The hydrogel of the cross polymer of Example 1a, and commercial HAs of 50 KDa and 250 KDa, displayed a viscous liquid character with G" being higher than G' under the conditions obtained. These results suggested that the hydrogel of the cross polymer from Example 1b, with a slightly higher cross-linking degree compared to that of Example 1a, provided a viscoelastic hydrogel not accessible with commercial and linear HA. Overall these results showed that surprisingly, by carefully controlling the conditions of cross-linking reaction and hence the composition of the final cross polymer, a fine tuning of the viscoelastic properties could be achieved.

Hydrogel from the cross polymer of Example 1b was further characterized at different concentrations of the cross polymer. All tested samples were found to exhibit viscoelastic behavior within the range of stresses applied, namely, the storage modulus (G') greater than the loss modulus (G"). As shown in Table 7 below, the storage modulus increased with the concentration so as the yield stress, where the viscoelastic character was lost due to the greater contribution of the loss modulus (G">G").

TABLE 7

Rheological parameters for the high cross-linking degree cross polymer of Example 1b at different concentrations and at 15° C.

| Concentration (% wt) | Yield Stress, $\sigma_y$ (Pa)$^a$ | G' (Pa)$^b$ |
|---|---|---|
| 0.5 | 0.8 | 1.3 |
| 1 | 1.6 | 3.1 |
| 2 | 4 | 5 |
| 3.5 | 20 | 14 |
| 5 | 30 | 24 |

$^a$Determined as the point where G' = G".
$^b$Determined at an oscillatory stress of 1 Pa.
"wt" stands for weight Data showed that under the conditions employed, the cross polymer of Example 1b showed a viscoelastic character (G">G"), whereas the cross polymer of Example 1a with a lower cross-linking degree and the commercial HA (250 KDa and 50 KDa) behaved as viscous liquids under the oscillatory experiments performed (see FIG. 7).

Example 5. Compatibility Assay of the Cross Polymers of the Invention with Cosmetic Formulations The compatibility of the cross polymers of the present invention with conventional cosmetic formulations was studied using a low viscosity O/W (oil in water) emulsion as a representative example of a conventional cosmetic formula. In particular, the cross polymer tested was that of Example 1b.

As a general procedure, oil and water phases were kept in a 80° C. bath (sea sand) during 15 min to ensure temperature homogeneity. The high cross-linking degree cross polymer of Example 1b was dissolved in the water phase and emulsifier was included in the oil phase. Water phase was placed in a 100 mL beaker, and stirred at 5,000 r.p.m. using a ultraturrax T25 equipped with a 25N-18G head. The oil phase was added to the previously obtained water phase over a period of 10 min after which the stirring was maintained while allowing to cooldown to RT to produce the cosmetic formulation to be tested. Table 7 below shows the relative quantities employed for its preparation. As shown in Table 7, in general, the addition of the cross polymer of Example 1b increased the viscosity of the tested formulation.

TABLE 8

| Formulation | [Cross polymer] (%) | Water (mL) | Sunflower oil (mL) | A&L | Viscosity (Pa · s)$^a$ |
|---|---|---|---|---|---|
| SV-YAL-27 | — | 32 | 16 | 1.00 | 2.3 |
| SV-YAL-28 | 0.25 | 32 | 16 | 0.75 | 3.3 |
| SV-YAL-29 | 0.50 | 32 | 16 | 0.75 | 4.5 |
| SV-YAL-30 | 0.75 | 32 | 16 | 0.75 | 5.1 |
| SV-YAL-32 | 1.00 | 32 | 16 | 0.75 | 9.0 |

Figure 8:
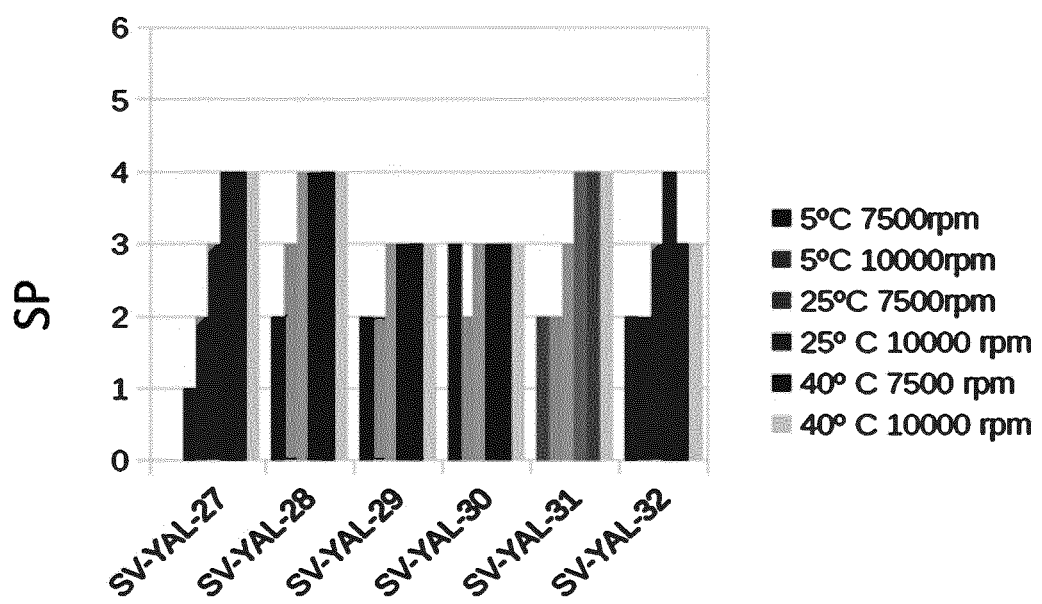
FIG. 8 shows the bar graph representing the separation degree of formulations comprising the cross polymer of the invention with conventional cosmetic formulations. "SP" stands for separation degree. "0" corresponds to no separation. "1" corresponds to minimum water phase appearance. "2-4" correspond to higher amount of water phase separated. "5" corresponds to complete phase separation in water emulsifier and oil.

$^a$measured at a shear rate of 1s$^{-1}$.
"A&L" stands for alcohol & lauryl sodium sulfate The forced stability of the cosmetic formulation was studied through centrifugation at different temperatures, ranging from 5 to 40° C., and at different r.p.m., ranging from 7,500 to 10,000 rpm. The incorporation of the cross polymer of Example 1.b increased the stability of the formulation against centrifuge force (see FIG. 8).

Example 6. Digestion of the Cross Polymers of the Invention with Hyaluronidase (HAase)

Figure 9:
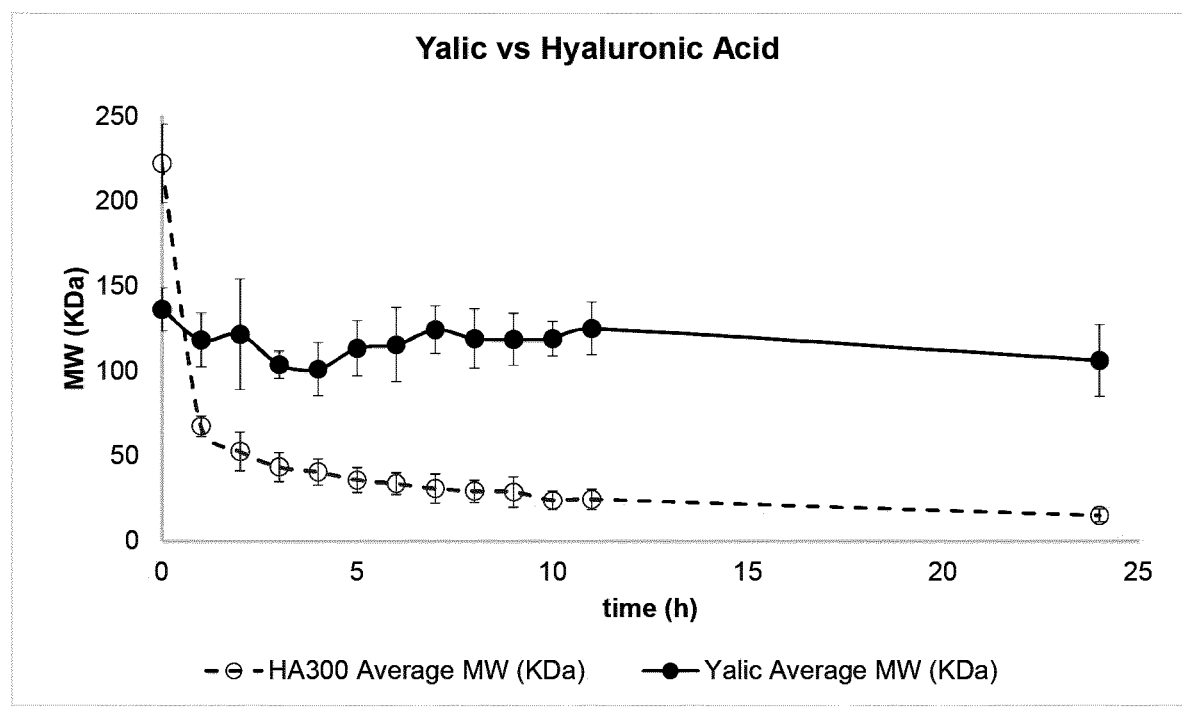
FIG. 9 shows the results of the digestion with hyaluronidase of the cross polymer of Example 1 b.

HAase degradation was studied via size-exclusion chromatography. Initially, 3.75 mg/mL of commercial HA (250 KDa) and the cross-polymer of Example 1b were independently incubated with hyaluronidase (0.005 mg/ml corresponding to 5 U/mL) at 37° C. inside the instrument Autosampler AF2000. Thirty µL of each sample were injected at the required time points. Determination of the MW was carried out with RI and MALS detection employing a do/dc determined from recovered mass. As shown in FIG. 9, determination of MW from SEC-RI-MALS revealed a fast degradation of commercial HA within the first 5 h resulting in a reduction of MW down to 35 KDa, while the MW of the cross polymer remained practically unaltered after 24 h treatment with HAase.

Example 7. Cross Polymers as Drug Delivery System: Human Skin Permeation Assays To study the potential of the cross-polymers of the present invention in topical applications, permeation studies were undertaken in human skin.

Example 7.1. Cross Polymers as Drug Delivery System of Polymeric Micelles

The influence of the cross-polymers solutions as platform for the formulation of polymeric micelles as drug delivery vehicles was evaluated.

Materials and Methods

Fluorescently labelled polymeric micelles were prepared from the commercial block copolymer Poloxamer® via co-solvent methodology. Briefly, the Poloxamer® (20 mg/ml) and the fluorescent dye (Dil-C18(3), 0.2 mg/mL) were dissolved in THF and added dropwise into MilliQ water with continuous stirring at RT until the evaporation of the organic solvent. The formulations were allowed to equilibrate at RT for 24 hours, followed by centrifugation at 1,000 rpm for 10 minutes. The supernatant was dialyzed against MilliQ water, MWCO=1,000 Da. The resulting fluorescently labelled polymeric micelles were independently formulated in MilliQ water and in a 3.75 mg/mL solution of the cross-polymer of Example 1a.

Skin Preparation

The skin permeation was studied using full thickness human skin obtained from a plastic surgery operation. To reduce inter-individual variability and afford better comparison of results, skin from only one donor was used in all experiments. The skin was cut into pieces (4×4 cm) suitable to be placed on a modified franz type diffusion cell. The skin covered with saline moistened filter paper wrapped in plastic film and with aluminum foil, was stored at ×20° C. until used. Before performing the assay, the subcutaneous fat was carefully removed by scalpel and the skin was allowed to come to RT.

Permeation Study

All skin permeation studies employed the modified franz type diffusion cell with a diffusional area of 0.95 cm$^2$. The skin was carefully mounted between the upper donor and the lower receiver compartments with the stratum corneal side up. The receptor chamber was then filled with 8 mL phosphate buffered saline (PBS, pH=7.4) with great care to avoid trapping air beneath the membrane, stirred at 600 r.p.m. at a thermostated temperature of 37° C. After an equilibration time of 30 min, 100 μL of each of the tested formulations was introduced into the donor compartment using a standard pipette. A fixed concentration of the formulations was used in all cases (10 mg/mL of fluorescently labelled polymeric micelles). The donor compartment was then sealed with Parafilm® and aluminum foil. The experiment was run for 24 hours. At predetermined time intervals, the entire receptor medium was withdrawn from the receiver compartment and replaced with equal volume of fresh buffer equilibrated to the experimental temperature (37° C.).

Skin Visualization Through Confocal Laser Scanning Microscopy

Figure 10:
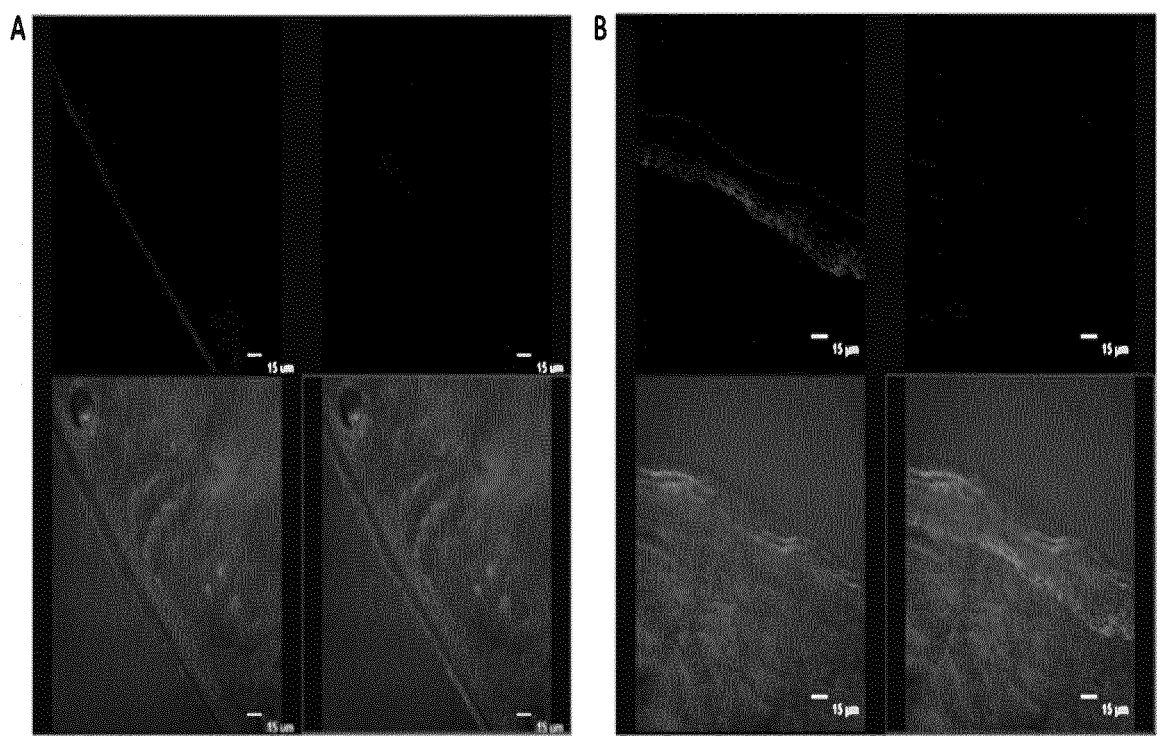
FIG. 10 shows the confocal laser scanning microscopy images of skin slices permeated with a solution of the cross polymer of the invention formulated with fluorescently labelled polymeric micelles.

Part of skin was fixed in 10% formalin for 24 h, followed by 30% sucrose in phosphate buffer. The skin was cryopreserved on dry ice then sliced using microtome into 10-micron thickness slices. The skin pieces were frozen at −20° C., 0.2 cm×0.5 cm piece from the treated area was cut out and embedded in optimal cutting temperature (OCT) compound. A cryostat (Leica Cryostat CM 3050S, Wetzlar, Germany) was used to prepare the vertical cross-sections of skin. Nine to twelve vertical sections of each sample with a thickness of 20 μm were obtained and stored at 4° C. till analyzed microscopically. The slices were placed on glass slides, fixed with formalin and stained with 6-diamidino-2-phenylindole (DAPI). Then examined under confocal laser scanning microscope. Dil-C18(3) was excited at λex=549 nm and detected at λem=566 nm and the fluorescent emission signals were represented by a red color. DAPI-stained cell nuclei were excited with the 405 nm line from blue diode. Polymeric micelles labelled with Dil-C18(3) dye (red) were found to accumulate preferentially into the stratum corneum when formulated in pure MilliQ water (FIG. 10A). In contrast, a clear enhancement in permeation into epidermis layer was observed in the presence of cross polymer as revealed by the increase of Dil-C18(3) florescence (red) in the epidermal region (keratinocyte's nucleus stained with DAPI, blue) (FIG. 10B).

Example 7.2. Cross Polymers as a Drug Delivery System of Conjugated Active Molecules Materials and Methods Cyanine 5.5 amine (Cy5.5) was purchased form Lumiprobe. Dimethyl sulfoxide (DMSO), sodium hydroxide and absolute ethanol (>99%) were obtained from Scharlab. Coupling agent 4-(4,6-Dimethoxy-1,3,5-triazin-2-yl)-4-methylmorpholinium chloride (DMTMMCl) was synthetized following conventional procedures known to the person skilled in the art. Vivaspin of MWCO of 100 KDa was purchased from Sartorius.

Conjugation Reaction

The cross polymer of Example 1b (401.33 g/mol by unit of sodium hyaluronate; 100.00 mg; 0.2492 mmol) was added to a round bottom flask of 50 mL and was dissolved in purified water type I (18 mL) at RT with magnetic stirrer. In parallel, in a vial with a magnetic stirrer coupling agent DMTMMCl (276.72 g/mol; 3.45 mg; 0.0125 mmol; 0.05 eq to hyaluronate) was dissolved in purified water type I (1.5 mL). The DMTMMCl solution was added to the solution of the cross polymer and the pH was adjusted to 7 with a few microliters of NaOH 1M. The coupling activation of carboxylic acid through DMTMMCl was allowed to proceed for 20-30 min. After that, a solution of Cy5.5 (753.88 g/mol; 1.88 mg; 0.0025 mmol; 0.01 eq to hyaluronate) previously prepared in DMSO (0.5 mL) and purified water type I (0.5 mL) was added and the pH was adjusted at 8.5 with a few μL of NaOH 1M. The resultant blue solution of the conjugation reaction of the cross polymer with the Cy5.5 was allowed to proceed for 72 hours at RT.

Conjugation Purification

After that, the conjugation solution was added into a vivaspin MWCO of 100 KDa and washed with 200 mL of PB 5 mM at pH 7.5 in order to remove the organic sub-products of the reaction (N-methylmorpholine (NMM), DMTMMCl and 2-chloro-4,6-dimethoxy-1,3,5-triazine (CDMT) and the DMSO. The resulting solution was washed again with 50 mL purified water type I to remove the PB salts. Then, the obtained solution was freeze dried and the resultant blue powder was washed five times with 45 mL per each of absolute ethanol and it was removed in vacuum. Finally, a dry blue powder was obtained.

Quantification of Cy5.5 by UV-Vis

Stock solution of Cy5.5 was prepared at 2.5 mg/mL in DMSO. A second stock solution of Cy5.5 in purified water type I was obtained at 0.025 mg/mL through stock solution of DMSO. The calibration curve was prepared using Cy5.5 as standard at increasing concentrations (0.05 to 0.25 μg/mL of Cy5.5) measuring the absorbance at λ=676 nm. Solutions of the cross polymer of Example 1b conjugated to Cy5.5 were prepared approx. at 0.10 μg/mL of Cy5.5 in purified water type II. Absorbance at λ=676 nm was measured and Cy5.5 loading within the cross-polymer determined to be 1.1% w/w.

Figure 11:
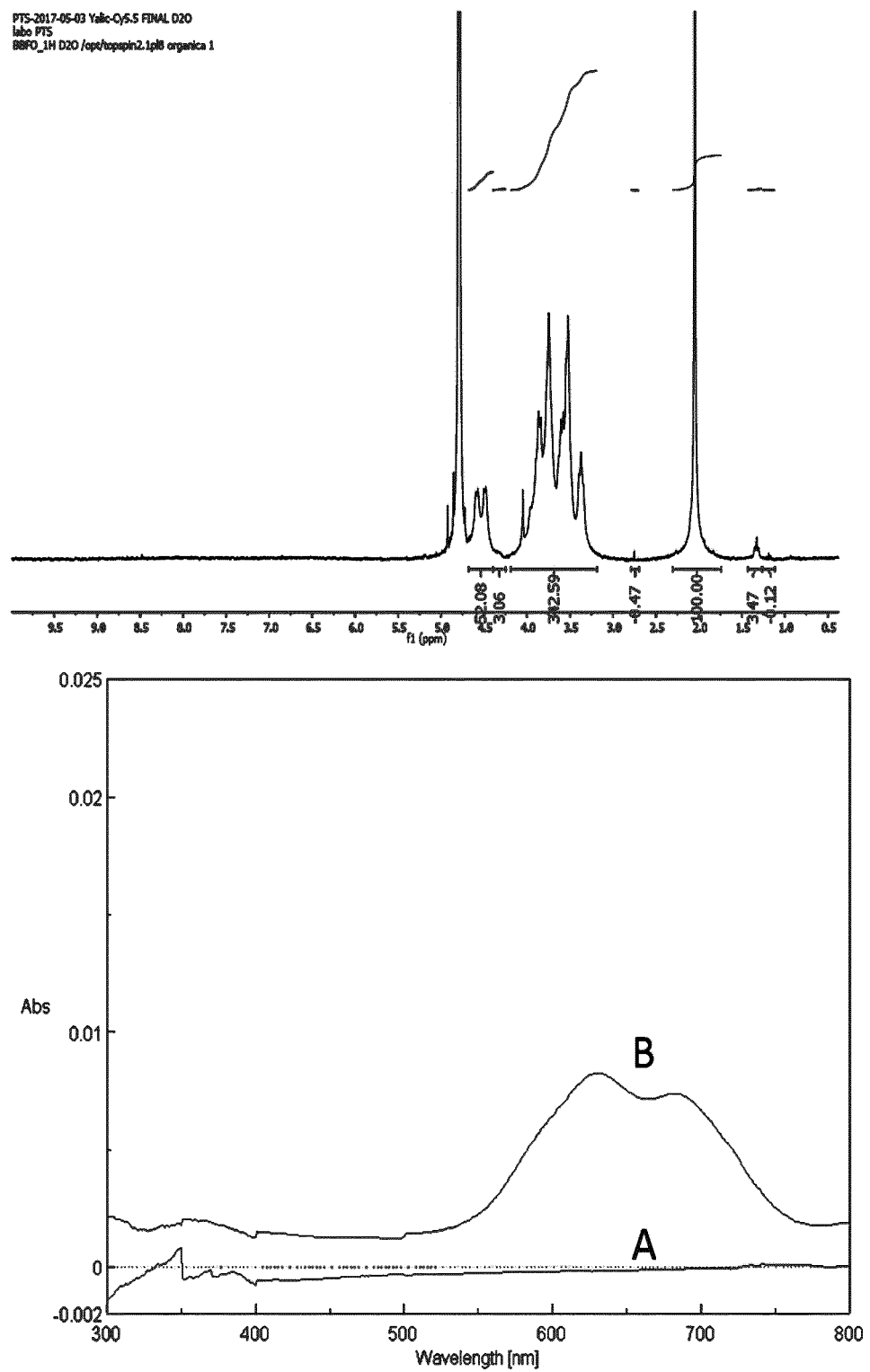
FIG. 11 shows the $^1$HNMR and UV-Vis spectra of the cross-polymer of Example 1b conjugated with —Cy5.5.
Figure 12:
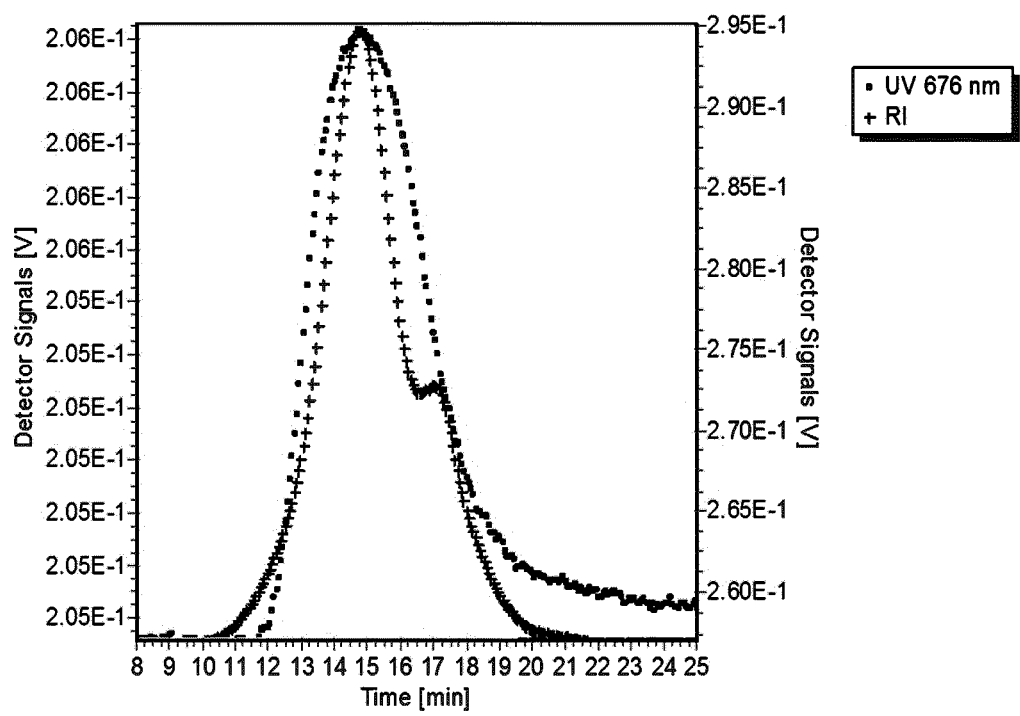
FIG. 12 shows the size-exclusion chromatography analysis of fluorescently labelled [HA]-[PGA]-[Lys] cross polymers obtained in Example 3 using Cyanine 5.5 with RI and UV (676 nm) detectors.

FIG. 11, shows the characterization of the conjugate of the cross-polymer of Example 1b with Cy5.5 by $^1$H NMR and UV-Vis. $^1$H NMR spectra showed the typical signals for the cross polymer of Example 1b, and the low Cy5.5. loading hinders the appropriate evaluation of Cy5.5 related $^1$H NMR signals. Nevertheless, UV analysis showed the presence of characteristic absorbance from Cy5.5 within the cross polymer-Cy5.5 conjugates. More importantly, FIG. 12 showed the size exclusion chromatograms of the cross polymer-Cy5.5 conjugates with RI and UV (676 nm) detectors showing the homogeneous presence of Cy5.5 along the cross polymer population and therefore confirming the identity and purity of the conjugate.

Table 9 below shows the MW determined by size exclusion chromatography for HA 50 KDa commercial, the cross polymer of Example 1b and the cross polymer-Cy5.5 conjugate. The results showed that the conjugation of the cross polymer with Cy5.5 slightly increases the MW of the corresponding cross polymer.

TABLE 9

| Compound | MW (KDa) | PDI |
|---|---|---|
| HA | 50.4 | 1.37 |
| Cross polymer of Example 1b | 145.7 | 1.37 |
| Conjugate of cross polymer of Example 1b and Cy5.5 | 186.2 | 1.41 |

Following the experimental methods described in Example 7.1, the cross polymer-Cy5.5 conjugate was evaluated for the topical delivery to skin through the permeation experiments described above using a concentration of 10 mg/ml conjugate in milliQ water.

Skin Visualization Through Confocal Laser Scanning Microscopy

Figure 13:
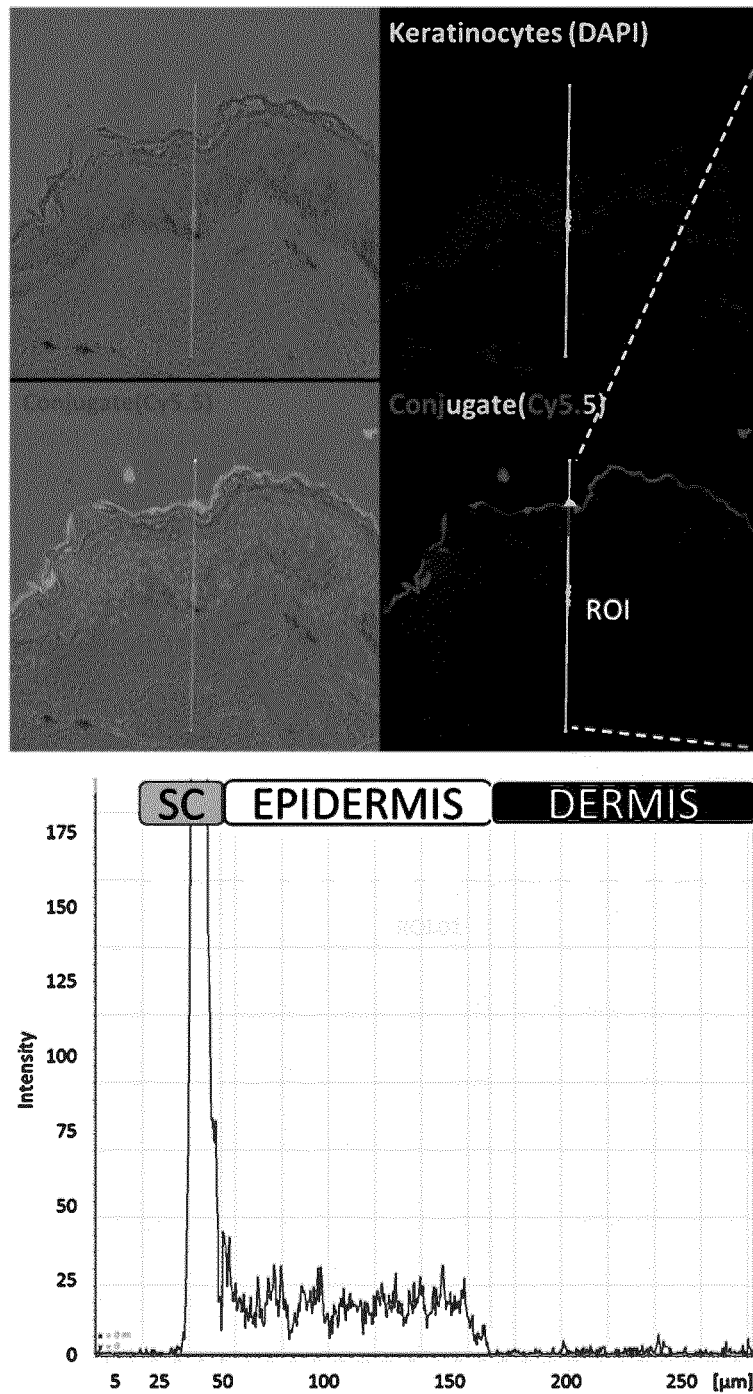
FIG. 13 shows the confocal laser scanning microscopy images of skin slices permeated with a solution of the fluorescently labelled cross polymer obtained in Example 3.

The skin was fixed in 10% formalin for 24 h, followed by 30% sucrose in phosphate buffer. Then the skin was cryo-preserved on dry ice then sliced using microtome into 10-micron thickness slices. The skin pieces were frozen at −20° C. Pieces of 0.2 cm×0.5 cm from the treated area was cut out and embedded in optimal cutting temperature (OCT) compound. A cryostat (Leica Cryostat CM 3050S, Wetzlar, Germany) was used to prepare the vertical cross-sections of the kin. Nine to twelve vertical sections of each sample with a thickness of 20 μm were obtained and stored at 4° C. till analyzed microscopically. The slices were placed on glass slides, fixed with formalin and stained with 6-diamidino-2-phenylindole (DAPI). Then examined under confocal laser scanning microscope. Cross polymer-Cy5.5 conjugate was excited at λex=676 nm and detected at λem=694 nm and the fluorescent emission signals were represented by a red color. DAPI-stained cell nuclei were excited with the 405 nm line from blue diode. Cross polymer-Cy5.5 conjugates were found to accumulate preferentially into the stratum corneum with a clear permeation into epidermis layer as shown in FIG. 13, suggesting that a reservoir of cross polymer at the stratum corneum layer was unexpectedly generated providing a sustained release of the cross polymers of the present invention to the epidermal layer.

Example 8. Cross Polymers as a Cell Culture Medium Component to Improve Cell Viability Cell Viability Study To carry out cell viability studies in vitro, fibroblasts were used. The culture media used were high Dulbecco's Modified Eagle's Medium-high glucose, supplemented with 2% penicillin/streptomycin and 50 mL of fetal bovine serum (FBS) in a humidified incubator 5% $CO_2$ and 37° C.

Procedure

Fifty μL of cells were seeded in 96-well plates at a concentration of 2,000 cells/well. After 24 hours, 50 μL of each treatment were added reaching a final volume of 100 μL in the well. All the treatments were filtered before adding to the well (pore size 0.45 μm). Cells were incubated with samples or controls for 72 hours and then was performed the MTS assay. For that, 20 μL of the solution of Phenazine Methosulfate Minimum 90% (PMS, Sigma, Spain) and salt of 3-(4,5-dimethylthiazol-2-yl)-5-(3-carboxymethylphenyl)-2-(4-sulfophenyl)-2H tetrazolium), (MTS, Promega, Spain) were added, with a dilution 1:20 respectively. After 3 hours of incubation, the absorbance was read at 490 nm using Victor2Wallac™ plate reader. The concentrations tested were in a range from 5 to 0.02 mg/ml for cross polymer obtained in Example 1a.

REFERENCES

1. LAVILLA C, BYRNE M and HEISE A. Block-sequence-specific polypeptides from α-amino acid N-carboxyanhydrides: synthesis and influence on polypeptide properties. Macromolecules 2016, Vol. 49 (8), pages 2941-2947.
2. ROBIN, Y. α-Amino acid N-carboxyanhydrides in pharmaceutical innovations. Chimica Oggi—Chemistry Today 2015, Vol. 33 (4), pages 26-31.
3. DENG C. et al. Functional polypeptide and hybrid materials: Precision synthesis via α-amino acid N-carboxyanhydride polymerization and emerging biomedical applications. Progress in Polymer Science 2014, Vol. 39, pages 330-364.
4. LU H. et al. Recent advances in amino acid N-carboxyanhydrides and synthetic polypeptides: chemistry, self-assembly and biological applications. Chem. Comm. 2014, Vol. 50, pages 139-155.
5. BARZ, M et al. A versatile post-polymerization modification method for polyglutamic acid: synthesis of orthogonal reactive polyglutamates and their use in "click chemistry". Polym. Chem. 2013, Vol. 4 (10), pages 2989-2994.

The invention claimed is:

1. A cross-polymer comprising two or more recurring units of formula (I) below:

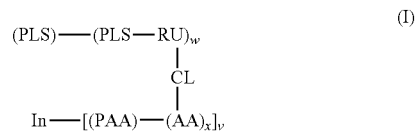

or its salt, solvate or isomer, wherein:

PLS is a radical of a polysaccharide;

PLS-RU is a radical of a repeating unit of the polysaccharide;

PAA is a radical of a polyamino acid comprising at least two amino acid units, wherein the polyamino acid is selected from the group consisting of homo-polyamino acids, random co-polyamino acids, and block co-polyamino acids, with the proviso that the homo-polyamino acid is not polycationic;

AA is a radical of an amino acid unit of the polyamino acid;

subscript x of the radical (AA) is an integer selected from 1 to 200;

subscript v of the radical [(PAA)-(AA)$_x$] is an integer selected from 1 to 48;

subscript w of the radical (PLS-RU) is an integer selected from 1 to 200;

In is a ROP initiator which comprises a terminal X group per each [(PAA)-(AA)] radical, wherein each terminal X group is directly bound to each [(PAA)-(AA)] radical, and wherein the terminal X group is selected from the group consisting of —NH—, —O—, —S—, and combinations thereof;

CL is a radical of a compound selected from the group consisting of ($C_1$-$C_{500}$)-alkyl, wherein two or more hydrogens are replaced by a moiety selected from (1) ($C_1$-$C_{500}$)-alkyl; (2) ($C_3$-$C_{30}$)-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) N(H)$NH_2$, (12) $R_gCOR_h$, (13) $COOR_i$, (14) CON($R_j$)

($R_k$), (15) $R_lN(R_m)CON(R_n)(R'_n)$, (16) ($C_1$-$C_{30}$)-alkenyl($C_1$-$C_{30}$)-alkene, (17) ($C_1$-$C_{30}$)-alkyne, (18) $N_3$, (19) $R_oCH(OR_p)(OR_q)$, (20) $R_rCH(SR_s)(SR_t)$, (21) $R_uB(OR_v)(OR_w)$, and (22) $COR_x$, wherein:

one or more carbons are optionally independently replaced by a moiety selected from ($C_3$-$C_{30}$)-cycloalkyl, aryl, aryl-($C_1$-$C_{30}$)-alkyl, $NR_yR_z$, CO, O, S, S(O), S($O_2$), B, P and (O—$CH_2$—$CH_2$)$_A$;

subscript A of the radical (O—$CH_2$—$CH_2$) is an integer selected from 1 to 500;

$R_a$, $R_b$, $R_c$, $R_d$, $R_e$, $R_f$, $R_h$, $R_i$, $R_j$, $R_k$, $R_m$, $R_n$, $R'_n$, $R_p$, $R_q$, $R_s$, $R_t$, $R_v$, $R_w$, $R_x$, $R_y$ and $R_z$ are radicals independently selected from the group consisting of H, ($C_1$-$C_{30}$)-alkyl, ($C_1$-$C_{30}$)-alkylphenyl, phenyl-($C_1$-$C_{30}$)-alkyl, and ($C_3$-$C_8$)-cycloalkyl, wherein one or more carbons are optionally independently replaced by a heteroatom selected from the group consisting of O, S, S(O), S($O_2$), halide, N, NH, P, and CO;

$R_g$, $R_l$, $R_o$, $R_r$ and $R_u$ are radicals independently selected from the group consisting of ($C_1$-$C_{30}$)-alkyl, ($C_1$-$C_{30}$)-alkylphenyl, phenyl-($C_1$-$C_{30}$)-alkyl, and ($C_3$-$C_8$)-cycloalkyl, wherein, one or more carbons are optionally independently replaced by a heteroatom selected from the group consisting of O, S, S(O), S($O_2$), halide, N, NH, P, and CO;

with the proviso that CL may be present or not present, wherein if CL is not present, the radical PLS-RU is directly bonded to a radical AA.

2. The cross polymer according to claim 1, wherein CL is not present.

3. The cross polymer according to claim 1, wherein CL is present.

4. The cross polymer according claim 1, wherein

PAA is a radical of formula (II)

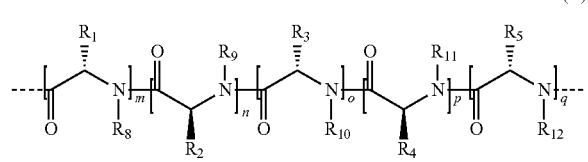

(II)

AA is a radical of formula (III)

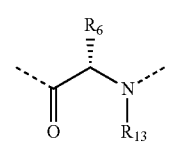

(III)

wherein m, n, o, p and q are integers independently selected from 0 to 500, and wherein m+n+o+p+q>1;

$R_1$ to $R_6$ are independently selected from the group consisting of:

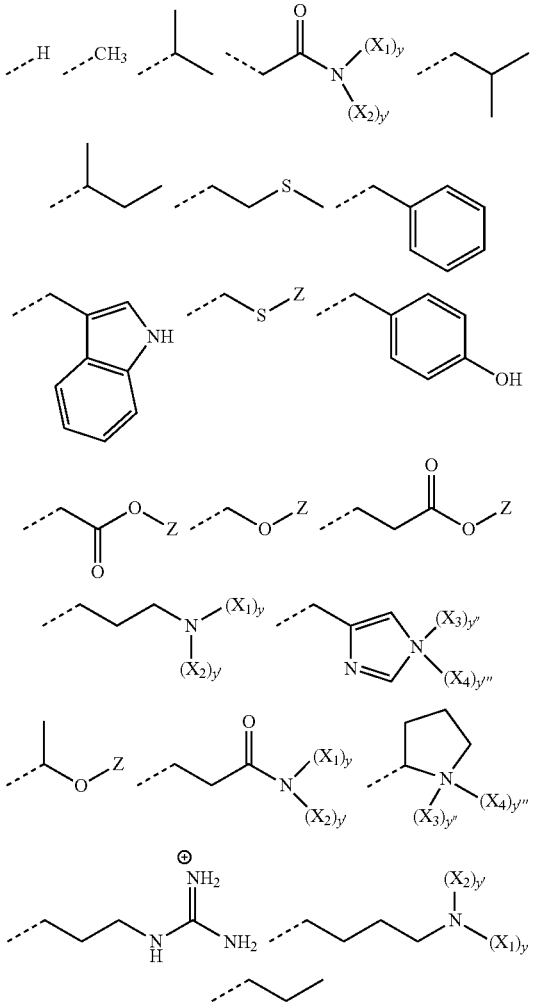

each $X_1$ and $X_2$ is independently selected from the group consisting of H, N, $NH_2$, and Z;

each $X_3$ and $X_4$ is independently selected from the group consisting of H and Z;

each y and y' is an integer independently selected from 0 to 3, wherein y+y'=2 or 3;

each y'' and y''' is an integer independently selected from 0 to 2, wherein y''+y'''=1 or 2;

Z is selected from the group consisting of H, metallic counterion and inorganic counterion; and $R_8$ to $R_{13}$ are independently selected from the group consisting of H and $C_1$-$C_4$ alkyl;

with the provisos that: (1) when CL is not present, a radical AA is bound through a peptide bond to the radical PAA through a terminal amine of the PAA radical; (2) when CL is present, a radical AA is bound to CL through a terminal amine of said radical AA, and (3) when a radical AA requires three points of attachment, one point of attachment is provided by $R_6$.

5. The cross polymer according to claim 1, wherein

PAA is a radical of formula (IV)

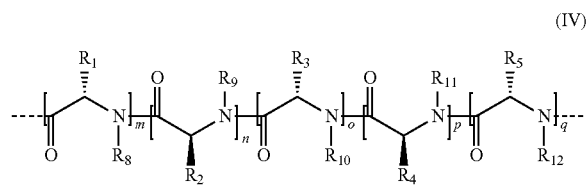

(IV)

AA is a radical of formula (V)

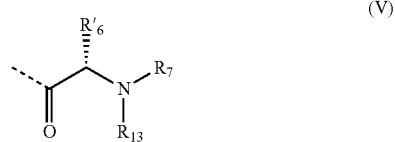

(V)

wherein m, n, o, p and q are integers independently selected from 0 to 500, and wherein m+n+o+p+q>1;

$R_1$ to $R_5$ are independently selected from the group consisting of:

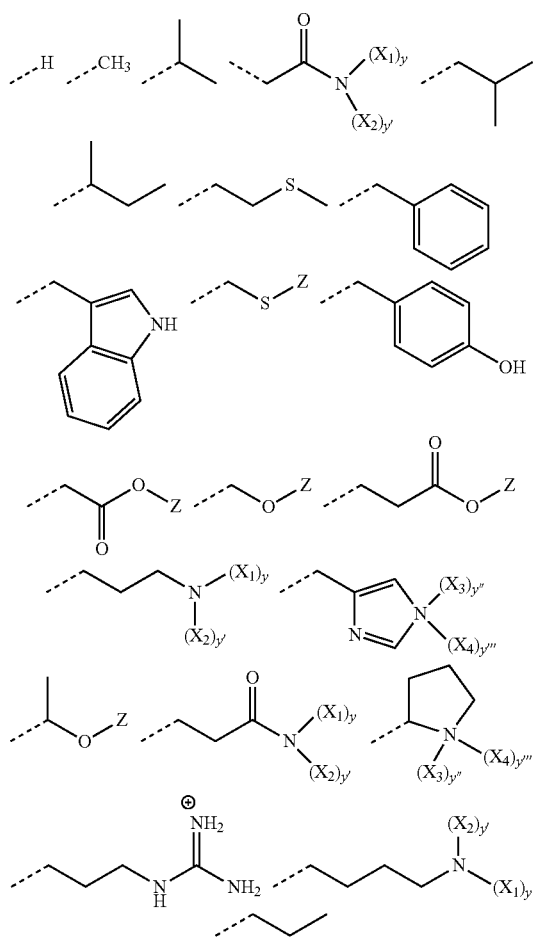

$R'_6$ is selected from the group consisting of:

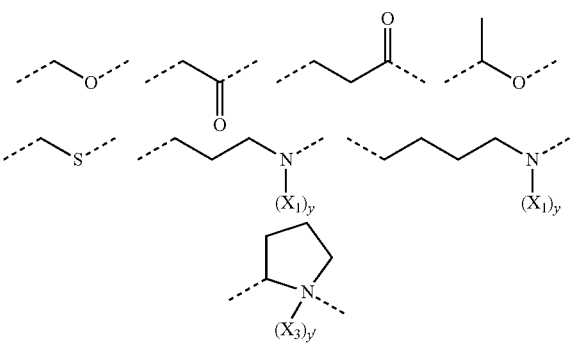

each $X_1$ and $X_2$ is independently selected from the group consisting of H, N, $NH_2$, and Z;

each $X_3$ and $X_4$ is independently selected from the group consisting of H and Z;

each subscript y and y' of $R_1$ to $R_5$ is an integer independently selected from 0 to 3, wherein y+y'=2 or 3;

each subscript y" and y''' of $R_1$ to $R_5$ is an integer independently selected from 0 to 2, wherein y"+y'''=1 or 2;

each subscript y of $R'_6$ is 1 or 2;

subscript y' of $R'_6$ is 0 or 1;

each Z is independently selected from the group consisting of H, metallic counterion and inorganic counterion;

$R_7$ is a radical selected from the group consisting of ($C_1$-$C_{500}$)-alkyl, wherein one or more hydrogens are replaced by a substituent selected from (1) ($C_1$-$C_{500}$)-alkyl; (2) ($C_3$-$C_{30}$)-cycloalkyl, (3) C-radical derived from a ring system with 1-6 rings, each ring being independently saturated, partially unsaturated or aromatic, the rings of the ring system being isolated or fused and each ring having 3-20 elements each element independently selected from the group consisting of C, CH, $CH_2$, CO, O, S, N and NH, (4) OH, (5) $NR_aR_b$, (6) $ONR_cR_d$, (7) CN, (8) halide, (9) $SH_2$, (10) $SR_eR_f$, (11) N(H)$NH_2$, (12) $R_gCOR_h$, (13) $COOR_i$, (14) CON($R_j$)($R_k$), (15) $R_lN(R_m)CON(R_n)(R'_n)$, (16) ($C_1$-$C_{30}$)-alkene, (17) ($C_1$-$C_{30}$)-alkyne, (18) $N_3$, (19) $R_oCH(OR_p)(OR_q)$, (20) $R_rCH(SR_s)(SR_t)$, (21) $R_uB(OR_v)(OR_w)$, and (22) CORN, wherein:

one or more carbons are optionally independently replaced by a moiety selected from ($C_3$-$C_{30}$)-cycloalkyl, aryl, aryl-($C_1$-$C_{30}$)-alkyl, $NR_yR_z$, CO, O, S, S(O), S($O_2$), B, P and (O—$CH_2$—$CH_2$)$_A$;

subscript A of the radical (O—$CH_2$—$CH_2$) is an integer selected from 1 to 500;

$R_a$, $R_b$, $R_c$, $R_d$, $R_e$, $R_f$, $R_h$, $R_i$, $R_j$, $R_k$, $R_m$, $R_n$, $R'_n$, $R_p$, $R_q$, $R_s$, $R_t$, $R_v$, $R_w$, $R_x$, $R_y$ and $R_z$ are radicals independently selected from the group consisting of H, ($C_1$-$C_{30}$)-alkyl, ($C_1$-$C_{30}$)-alkylphenyl, phenyl ($C_1$-$C_{30}$)-alkyl and ($C_3$-$C_8$)-cycloalkyl, wherein one or more carbons are optionally independently replaced by a heteroatom selected from the group consisting of O, S, S(O), S($O_2$), halide, N, NH, P, and CO;

$R_g$, $R_l$, $R_o$, $R_r$ and $R_u$ are radicals independently selected from the group consisting of ($C_1$-$C_{30}$)-alkyl, ($C_1$-$C_{30}$)-alkylphenyl, phenyl, ($C_1$-$C_{30}$)-alkyl, and ($C_3$-$C_8$)-cycloalkyl, wherein one or more carbons are optionally independently replaced by a heteroatom selected from the group consisting of O, S, S(O), S($O_2$), halide, N, NH, P, and CO; and $R_8$ to $R_{13}$ are independently selected from the group consisting of H and ($C_1$-$C_4$)-alkyl;

with the provisos that: (1) when CL is not present, a radical AA is bound through a peptide bond to the radical PAA through a terminal amine of the radical PAA; and (2) when CL is present, a radical AA is bound to CL through R'$_6$.

6. The cross polymer according to claim 4, wherein $R_1=R_2=R_3=R_4=R_5=R_6$.

7. The cross polymer according to claim 5, wherein $R_1=R_2=R_3=R_4=R_5$ and R'$_6$ is the corresponding double radical of said $R_1=R_2=R_3=R_4=R_5$.

8. The cross polymer according to claim 4, wherein the polyamino acid is a random or block co-polyamino acid.

9. The cross polymer according to claim 8, wherein $R_1$, $R_2$, $R_3$, $R_4$, $R_5$ and $R_6$ are independently selected from the group consisting of:

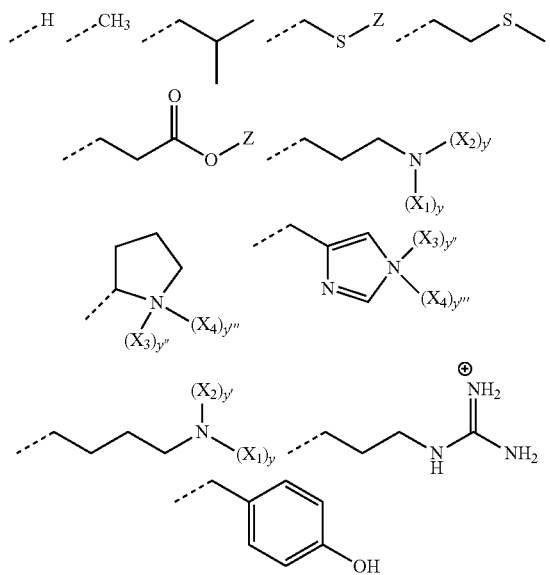

wherein
each $X_1$ and $X_2$ is independently selected from the group consisting of H, N, $NH_2$, and Z;
each $X_3$ and $X_4$ is independently selected from the group consisting of H and Z;
each y and y' is an integer independently selected from 0 to 3, wherein y+y'=2 or 3;
each y" and y''' is an integer independently selected from 0 to 2, wherein y"+y'''=1 or 2; and
Z is selected from the group consisting of H, metallic counterion and inorganic counterion.

10. The cross polymer according to claim 5, wherein the polyamino acid is a random or block co-polyamino acid.

11. The cross polymer according to claim 10, wherein $R_1$ to $R_5$ are independently selected from the group consisting of:

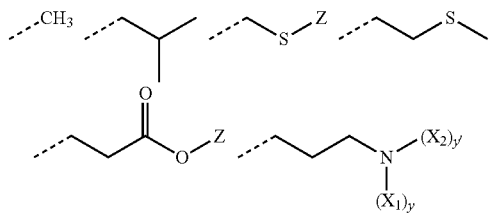
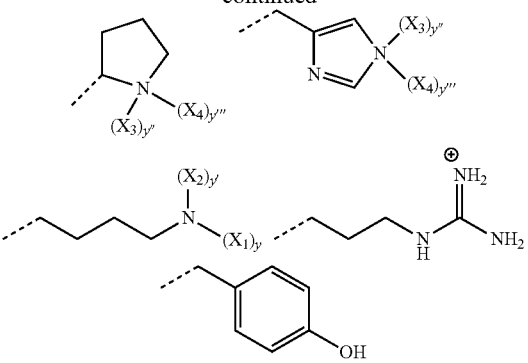

R'$_6$ is selected from the group consisting of:

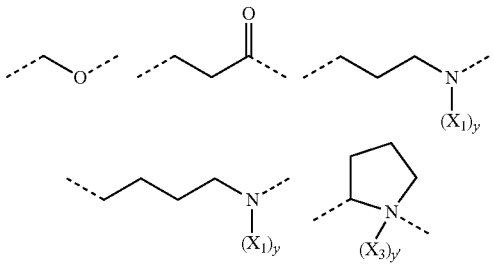

wherein
each $X_1$ and $X_2$ is independently selected from the group consisting of H, N, $NH_2$, and Z;
each $X_3$ and $X_4$ is independently selected from the group consisting of H and Z;
each y and y' is an integer independently selected from 0 to 3, wherein y+y'=2 or 3;
each y" and y''' is an integer independently selected from 0 to 2, wherein y"+y'''=1 or 2; and
Z is selected from the group consisting of H, metallic counterion and inorganic counterion.

12. The cross polymer according to claim 2, wherein the polysaccharide is hyaluronic acid, PAA is polyglutamate, AA is glutamate, v is an integer selected from 2 to 4, and x+w is an integer selected from 2 to 200.

13. The cross polymer according to claim 3, wherein the polysaccharide is hyaluronic acid, PAA is polyglutamate, AA is glutamate, v=1, x+w is an integer selected from 2 to 200 and CL is —NH—CH(COOH)—($C_1$-$C_4$)-alkyl-NH—.

14. A conjugate comprising the cross polymer according to claim 1 and at least one active agent bound to the cross polymer.

15. The conjugate according to claim 14, wherein the at one least active agent is selected from the group consisting of an active pharmaceutical agent, an imaging agent, an active pharmaceutical agent and an imaging agent, and a cosmetic agent.

16. A pharmaceutical, diagnostic or theranostic composition comprising (i) at least one conjugate according to claim 15, wherein the at least one active agent is selected from the group consisting of an active pharmaceutical agent, an imaging agent, and combinations thereof, and (ii) one or more pharmaceutically, diagnostically or theranostically acceptable excipients or carriers.

17. A conjugate according to claim 15, wherein the at least one active agent is selected from the group consisting of an active pharmaceutical agent, and an active pharmaceutical agent and an imaging agent.

18. A conjugate according to claim 15, wherein the at least one active agent is selected from the group consisting of an active pharmaceutical agent and an imaging agent, and an imaging agent.

19. A (dermo-)cosmetic composition comprising (i) a conjugate according to claim 4, wherein the at least one active agent is a cosmetic agent, and (ii) one or more cosmetically acceptable excipients.

* * * * *